US012778991B2

(12) United States Patent
Kim et al.

(10) Patent No.: US 12,778,991 B2
(45) Date of Patent: *Nov. 3, 2026

(54) METHOD OF TREATMENT WITH LACTIC ACID BACTERIA

(71) Applicants: UNIVERSITY-INDUSTRY COOPERATION GROUP OF KYUNG HEE UNIVERSITY, Gyeonggi-do (KR); NAVIPHARM CO., LTD., Gyeonggi-do (KR)

(72) Inventors: Dong-Hyun Kim, Seoul (KR); Myung Joo Han, Seoul (KR)

(73) Assignees: UNIVERSITY-INDUSTRY COOPERATION GROUP OF KYUNG HEE UNIVERSITY, Gyeonggi-do (KR); NAVIPHARM CO., LTD., Gyeonggi-do (KR)

( * ) Notice: Subject to any disclaimer, the term of this patent is extended or adjusted under 35 U.S.C. 154(b) by 648 days.

This patent is subject to a terminal disclaimer.

(21) Appl. No.: 18/137,541

(22) Filed: Apr. 21, 2023

(65) Prior Publication Data

US 2023/0355690 A1 Nov. 9, 2023

Related U.S. Application Data

(63) Continuation of application No. 16/481,643, filed as application No. PCT/KR2018/001359 on Jan. 31, 2018, now Pat. No. 11,660,321.

(30) Foreign Application Priority Data

Jan. 31, 2017 (KR) ........................ 10-2017-0013632

(51) Int. Cl.

| | |
|---|---|
| ***A61K 35/745*** | (2015.01) |
| ***A21D 8/04*** | (2006.01) |
| ***A23C 9/127*** | (2006.01) |
| ***A23L 2/02*** | (2006.01) |
| ***A23L 2/52*** | (2006.01) |
| ***A23L 7/104*** | (2016.01) |
| ***A23L 33/135*** | (2016.01) |
| ***A61K 35/00*** | (2006.01) |
| ***A61K 35/747*** | (2015.01) |
| ***A61P 29/00*** | (2006.01) |
| ***A61P 37/06*** | (2006.01) |
| ***A61P 37/08*** | (2006.01) |
| ***C12N 1/205*** | (2026.01) |
| ***C12R 1/25*** | (2006.01) |

(52) U.S. Cl.

CPC .............. *A61K 35/745* (2013.01); *A21D 8/04* (2013.01); *A23C 9/127* (2013.01); *A23L 2/02* (2013.01); *A23L 2/52* (2013.01); *A23L 7/104* (2016.08); *A23L 33/135* (2016.08); *A61K 35/747* (2013.01); *A61P 29/00* (2018.01); *A61P 37/06* (2018.01); *A61P 37/08* (2018.01); *C12N 1/205* (2021.05); *A23V 2002/00* (2013.01); *A23V 2400/169* (2023.08); *A23V 2400/533* (2023.08); *A61K 2035/115* (2013.01); *C12R 2001/25* (2021.05)

(58) Field of Classification Search

CPC ..... A23L 33/135; A61K 35/747; A61P 29/00; A61P 37/06; A61P 37/08; A23V 2400/169; C12R 2001/25

See application file for complete search history.

(56) References Cited

U.S. PATENT DOCUMENTS

| | | | | |
|---|---|---|---|---|
| 8,557,233 | B2 | 10/2013 | MacSharry et al. | |
| 8,936,783 | B2 | 1/2015 | Alenfall et al. | |
| 9,456,630 | B2 | 10/2016 | Mercenier et al. | |
| 9,956,282 | B2 * | 5/2018 | Cook | A61K 49/0004 |
| 11,202,811 | B2 * | 12/2021 | Kim | A61P 17/06 |
| 2010/0092440 | A1 * | 4/2010 | Strozzi | A61P 31/00 424/93.46 |
| 2010/0310513 | A1 | 12/2010 | Daube et al. | |
| 2012/0201785 | A1 | 8/2012 | Mercenier et al. | |
| 2012/0208260 | A1 | 8/2012 | Kim et al. | |

(Continued)

FOREIGN PATENT DOCUMENTS

| | | | |
|---|---|---|---|
| CN | 101744841 | A | 6/2010 |
| CN | 102946891 | A | 2/2013 |

(Continued)

OTHER PUBLICATIONS

Chatzantoni et al., "Anti-TNF-a Antibody Therapies in Autoimmune Diseases," Current Topics in Medicinal Chemistry, 2006, 6:1707-1714.
Hirohata, "Human Thl responses driven by IL-12 are associated with enhanced expression of CD40 ligand," Clinical & Experimental Immunology. 1999, 115(1):78-85.
Jang et al., "The Role of Tumor Necrosis Factor Alpha (TNF-a) in Autoimmune Disease and Current TNF-a Inhibitors in Therapeutics," International Journal of Molecular Sciences, 2021, 22(5):2719.
Platzer et al., "Up-regulation of monocytic IL-10 by tumor necrosis factor-a and cAMP elevating drugs," International Immunology, 1995, 7(4):517-523.

(Continued)

*Primary Examiner* — Louise W Humphrey
*Assistant Examiner* — Alexander M Duryee
(74) *Attorney, Agent, or Firm* — Harness, Dickey & Pierce, P.L.C.

(57) ABSTRACT

A particular *Bifidobacterium* spp. strain or particular *Lactobacillus* spp. strain according to the present invention is isolated from excrement of a human or cabbage kimchi, and thus is highly safe and has physiological activities such as an immunity regulatory effect and an inflammation reaction inhibiting effect. Therefore, the particular *Bifidobacterium* spp. strain or particular *Lactobacillus* spp. strain according to the present invention may be used as a material for regulating immunity and inhibiting inflammation reactions, and may be also used as a functional food and drug material useful for preventing, alleviating or treating rhinitis, atopy, asthma, etc. which are allergic diseases.

14 Claims, 30 Drawing Sheets

Specification includes a Sequence Listing.

(56) References Cited

U.S. PATENT DOCUMENTS

| | | | |
|---|---|---|---|
| 2013/0045291 | A1 | 2/2013 | Tobita et al. |
| 2015/0240200 | A1 | 8/2015 | Tsai et al. |

FOREIGN PATENT DOCUMENTS

| | | | |
|---|---|---|---|
| CN | 104784219 | A | 7/2015 |
| CN | 106262931 | A | 1/2017 |
| EP | 2868206 | A2 | 5/2015 |
| JP | 2006273852 | A | 10/2006 |
| JP | 2016-136890 | A | 8/2016 |
| KR | 20050076374 | A | 7/2005 |
| KR | 2008-0075971 | A | 8/2008 |
| KR | 2008-0080981 | A | 9/2008 |
| KR | 2010-0016012 | A | 2/2010 |
| KR | 2011-0046020 | A | 5/2011 |
| KR | 10-2013-0034764 | A | 4/2013 |
| KR | 10-1482661 | B1 | 1/2015 |
| KR | 2015-0034243 | A | 4/2015 |
| KR | 2016-0069733 | A | 6/2016 |
| KR | 2016-0084823 | A | 7/2016 |
| KR | 101750468 | B1 | 6/2017 |
| RU | 2445362 | C2 | 3/2012 |
| RU | 2563525 | C2 | 9/2015 |
| WO | WO-2007/040444 | A1 | 4/2007 |
| WO | WO-2007/040446 | A1 | 4/2007 |
| WO | WO-2008/117266 | A2 | 10/2008 |
| WO | WO-2011/052996 | A2 | 5/2011 |
| WO | WO-2013/191342 | A1 | 12/2013 |
| WO | WO-2015/122717 | A1 | 8/2015 |

OTHER PUBLICATIONS

Zhang et al., "Therapeutic potential of TNFa inhibitors in chronic inflammatory disorders: Past and future," Genes & Diseases, 2021, 8(1):38-47.
EP Extended European Search Report in International Appln. No. 18748804.4, dated Nov. 16, 2020, 8 pages.
Gueniche et al., "Bifidobacterium longrnn lysate, a new ingredient for reactive skin," Experimental Dermatology, 2009, 19:el-e8.
RU Office Action in Russian Appln. No. 2019127021/10(052969), dated Nov. 30, 2020, 11 pages (with English translation).
Tarann1l, "Explanatory Biotechnological Dictionary," Timofeev (ed.), 2009, p. 104-105 and 308 (with English Translation).
International Search Report for PCT/KR2018/001359 mailed on May 21, 2018 (7 pages).
Bresson, et al., "LACTORAL and Living Probiotic Bacteria", The EFSA Journal, 2008, vol. 862, pp. 1-8. (9 pages).
Bifidobacterium longum BBMN68-specific modulated dendritic cells alleviate allergic responses to bovine ??-actoglobulin in mice, Yang, et al., Journal of Applied Microbiology, vol. 119, 2015, pp. 1127-1137. (11 pages).
Pffice Action issued on Mar. 20, 2019 for KR10-2018-0012186 and English translation (11 pages).
JP Office Action for Pat App No. 2019-541313, dated Jul. 28, 2020 (with English Translation) (13 pages).
RU Office Action for Pat App No. 20 I 9127021/10(052969), dated Jul. 2, 2020 (with English Translation) (16 pages).
RU Office Action in Russian Appln. No. 2021118078, dated Jan. 19, 2022, 12 pages (with English Translation).
JP Office Action in Japanese Appln. No. 2021-020363, dated Feb. 1, 2022, 9 pages (with English Translation).
IN Office Action in Indian Appln. No. 201947032509, dated Feb. 14, 2022, 6 pages (with English Translation).
Lee, In Hoe, et al., "Effects of Pro biotic Extracts of limchi on Immune Function in NC/Nga Mice", Korean J. Food Sci. Technol. 40(1): 82-87 (2008).
Office Action from corresponding U.S. Appl. No. 16/481,643, dated Aug. 19, 2022.
Notice of Allowance from corresponding U.S. Appl. No. 16/481,643, dated Jan. 20, 2023.
Office Action for Brazilian Patent Application No. BR 11 2019 015806 5, dated Feb. 16, 2024.
Liu, Y., et al.; "Oral Administration of Heat-Inactivated Lactobacillus plantarum K37 Modulated Airway Hyperresponsiveness in Ovalbumin-Sensitized BALB/c Mice", PLOS ONE, vol. 9 No. 6, p. 1-11, Jun. 17, 2014.
Takeda, S., et al.; "Antiallergic activity of probiotics from Mongolian dairy products on type I allergy in mice and mode of antiallergic action", Journal of Functional Foods, vol. 9, p. 60-69, Jul. 31, 2014.
Hijova, E., et al.; "Preventive use of Lactobacillus plantarum LS/07 and inulin to relieve symptoms of acute colitis", Acta Biochimica Polonica, vol. 62, No. 3, p. 553-557, Sep. 8, 2015.
Office Action from corresponding Chinese Patent Application No. 2023106349640, dated Jun. 2, 2026.

* cited by examiner

SEQUENCE LISTING

```
Sequence total quantity: 30
SEQ ID NO: 1            moltype = DNA  length = 1377
FEATURE                 Location/Qualifiers
source                  1..1377
                        mol_type = other DNA
                        organism = synthetic construct
SEQUENCE: 1
gacttgacgg ggcggtgtgt acaaggcccg ggaaacgcat tcaccgcgac gttgctgatt  60
cgcgattact agcgactccg ccttcacgca gtcgagttgc agactgcgat ccgaactgag  120
accggttttc agggatccgc tccgcgtcgc cgcgtcgcat cccgttgtac cggccattgt  180
agcatgcgtg aagccctgga cgtaaggggc atgatgatct gacgtcatcc ccaccttcct  240
ccgagttaac cccggcggtc ccccgtgagt tcccggcata atccgctggc aacacggggc  300
gagggttgcg ctcgttgcgg gacttaaccc aacatctcac gacacgagct gacgacgacc  360
atgcaccacc tgtgaacccg ccccgaaggg aagccgtatc tctacgaccg tcgggaacat  420
gtcaagccca ggtaaggttc ttcgcgttgc atcgaattaa tccgcatgct ccgccgcttg  480
tgcgggcccc cgtcaatttc tttgagtttt agccttgcgg ccgtactccc caggcgggat  540
gcttaacgcg ttagctccga cacggaaccc gtggaacggg ccccacatcc agcatccacc  600
gtttacggcg tggactacca gggtatctaa tcctgttcgc tccccacgct ttcgctcctc  660
agcgtcagta acggcccaga gacctgcctt cgccattggt gttcttcccg atatctacac  720
attccaccgt tacaccggga attccagtct cccctaccgc actcaagccc gcccgtaccc  780
ggcgcggatc caccgttaag cgatggactt tcacaccgga cgcgacgaac cgcctacgag  840
ccctttacgc ccaataattc cggataacgc ttgcacccta cgtattaccg cggctgctgg  900
cacgtagtta gccggtgctt attcaacggg taaactcact ctcgcttgct ccccgataaa  960
agaggtttac aacccgaagg cctccatccc tcacgcggcg tcgctgcatc aggcttgcgc  1020
ccattgtgca atattcccca ctgctgcctc ccgtaggagt ctgggccgta tctcagtccc  1080
aatgtggccg gtcgccctct caggccggct acccgtcgaa gccacggtgg gccgttaccc  1140
cgccgtcaag ctgataggac gcgaccccat cccataccgc gaaagctttc ccagaagacc  1200
atgcgatcaa ctggagcatc cggcattacc acccgtttcc aggagctatt ccggtgtatg  1260
gggcaggtcg gtcacgcatt actcacccgt tcgccactct caccaccaag caaagcccga  1320
tggatcccgt tcgacttgca tgtgttaagc acgccgccag cgttcatcct gagccat     1377
```

```
SEQ ID NO: 2           moltype = DNA  length = 1421
FEATURE                Location/Qualifiers
source                 1..1421
                       mol_type = other DNA
                       organism = synthetic construct
SEQUENCE: 2
ctggtattga ttggtgcttg catcatgatt tacatttgag tgagtggcga actggtgagt  60
aacacgtggg aaacctgccc agaagcgggg gataacacct ggaaacagat gctaataccg  120
cataacaact tggaccgcat ggtccgagct tgaaagatgg cttcggctat cacttttgga  180
tggtcccgcg gcgtattagc tagatggtgg ggtaacggct caccatggca atgatacgta  240
gccgacctga gagggtaatc ggccacattg ggactgagac acggcccaaa ctcctacggg  300
aggcagcagt agggaatctt ccacaatgga cgaaagtctg atggagcaac gccgcgtgag  360
tgaagaaggg tttcggctcg taaaactctg ttgttaaaga agaacatatc tgagagtaac  420
tgttcaggta ttgacggtat ttaaccagaa agccacggct aactacgtgc cagcagccgc  480
ggtaatacgt aggtggcaag cgttgtccgg gatttattgg gcgtaaagcg agcgcaggcg  540
gtttttttaag tctgatgtga aagccttcgg ctcaaccgaa gaagtgcatc ggaaactggg  600
aaacttgagt gcagaagagg acagtggaac tccatgtgta gcggtgaaat gcgtagatat  660
atggaagaac accagtggcg aaggcggctg tctggtctgt aactgacgct gaggctcgaa  720
agtatgggta gcaaacagga ttagataccc tggtagtcca taccgtaaac gatgaatgct  780
aagtgttgga gggtttccgc ccttcagtgc tgcagctaac gcattaagca ttccgcctgg  840
ggagtacggc cgcaaggctg aaactcaaag gaattgacgg gggcccgcac aagcggtgga  900
gcatgtggtt taattcgaag ctacgcgaag aaccttacca ggtcttgaca tactatgcaa  960
atctaagaga ttagacgttc ccttcgggga catggataca ggtggtgcat ggttgtcgtc  1020
agctcgtgtc gtgagatgtt gggttaagtc ccgcaacgag cgcaaccctt attatcagtt  1080
gccagcatta agttgggcac tctggtgaga ctgccggtga caaaccggag gaaggtgggg  1140
atgacgtcaa atcatcatgc cccttatgac ctgggctaca cacgtgctac aatggatggt  1200
acaacgagtt gcgaactcgc gagagtaagc taatctctta aagccattct cagttcggat  1260
tgtaggctgc aactcgccta catgaagtcg gaatcgctag taatcgcgga tcagcatgcc  1320
gcggtgaata cgttcccggg ccttgtacac accgcccgtc acaccatgag agtttgtaac  1380
acccaaagtc ggtggggtaa ccttttagga accagccgcc t                    1421

SEQ ID NO: 3           moltype = DNA  length = 22
FEATURE                Location/Qualifiers
source                 1..22
                       mol_type = other DNA
                       organism = synthetic construct
SEQUENCE: 3
cctcttctat ccaaccagta tc                                         22

SEQ ID NO: 4           moltype = DNA  length = 19
FEATURE                Location/Qualifiers
source                 1..19
                       mol_type = other DNA
                       organism = synthetic construct
SEQUENCE: 4
ctccgcttca taactgtgt                                             19

SEQ ID NO: 5           moltype = DNA  length = 24
FEATURE                Location/Qualifiers
source                 1..24
                       mol_type = other DNA
                       organism = synthetic construct
SEQUENCE: 5
tcaagtggca tagatgtgga agaa                                       24

SEQ ID NO: 6           moltype = DNA  length = 21
FEATURE                Location/Qualifiers
source                 1..21
                       mol_type = other DNA
                       organism = synthetic construct
SEQUENCE: 6
tggctctgca ggattttcat g                                          21

SEQ ID NO: 7           moltype = DNA  length = 21
FEATURE                Location/Qualifiers
source                 1..21
                       mol_type = other DNA
                       organism = synthetic construct
SEQUENCE: 7
gaaggcatcc agacccgaaa c                                          21

SEQ ID NO: 8           moltype = DNA  length = 20
FEATURE                Location/Qualifiers
source                 1..20
                       mol_type = other DNA
                       organism = synthetic construct
SEQUENCE: 8
acccatggcg gtgaccatgc                                            20
```

```
SEQ ID NO: 9           moltype = DNA  length = 25
FEATURE                Location/Qualifiers
source                 1..25
                       mol_type = other DNA
                       organism = synthetic construct
SEQUENCE: 9
aaagagaagt gtggcgagga gagac                                            25

SEQ ID NO: 10          moltype = DNA  length = 27
FEATURE                Location/Qualifiers
source                 1..27
                       mol_type = other DNA
                       organism = synthetic construct
SEQUENCE: 10
ccttccattg cccactctgt actcatc                                          27

SEQ ID NO: 11          moltype = DNA  length = 22
FEATURE                Location/Qualifiers
source                 1..22
                       mol_type = other DNA
                       organism = synthetic construct
SEQUENCE: 11
acagccactg cattcccagt tt                                               22

SEQ ID NO: 12          moltype = DNA  length = 22
FEATURE                Location/Qualifiers
source                 1..22
                       mol_type = other DNA
                       organism = synthetic construct
SEQUENCE: 12
tctcggaagg acttgcagac at                                               22

SEQ ID NO: 13          moltype = DNA  length = 21
FEATURE                Location/Qualifiers
source                 1..21
                       mol_type = other DNA
                       organism = synthetic construct
SEQUENCE: 13
tttaactccc ttggcgcaaa a                                                21

SEQ ID NO: 14          moltype = DNA  length = 20
FEATURE                Location/Qualifiers
source                 1..20
                       mol_type = other DNA
                       organism = synthetic construct
SEQUENCE: 14
ctttccctcc gcattgacac                                                  20

SEQ ID NO: 15          moltype = DNA  length = 18
FEATURE                Location/Qualifiers
source                 1..18
                       mol_type = other DNA
                       organism = synthetic construct
SEQUENCE: 15
cccatcccca ggagtctt                                                    18

SEQ ID NO: 16          moltype = DNA  length = 21
FEATURE                Location/Qualifiers
source                 1..21
                       mol_type = other DNA
                       organism = synthetic construct
SEQUENCE: 16
accatgacta ggggcactgt a                                                21

SEQ ID NO: 17          moltype = DNA  length = 23
FEATURE                Location/Qualifiers
source                 1..23
                       mol_type = other DNA
                       organism = synthetic construct
SEQUENCE: 17
atgctgcctg ctcttactga ctg                                              23

SEQ ID NO: 18          moltype = DNA  length = 24
FEATURE                Location/Qualifiers
source                 1..24
                       mol_type = other DNA
                       organism = synthetic construct
SEQUENCE: 18
```

```
cccaagtaac ccttaaagtc ctgc                                              24

SEQ ID NO: 19          moltype = DNA  length = 20
FEATURE                Location/Qualifiers
source                 1..20
                       mol_type = other DNA
                       organism = synthetic construct
SEQUENCE: 19
tgcagtggca aagtggagat                                                   20

SEQ ID NO: 20          moltype = DNA  length = 20
FEATURE                Location/Qualifiers
source                 1..20
                       mol_type = other DNA
                       organism = synthetic construct
SEQUENCE: 20
tttgccgtga gtggagtcat                                                   20

SEQ ID NO: 21          moltype = DNA  length = 25
FEATURE                Location/Qualifiers
source                 1..25
                       mol_type = other DNA
                       organism = synthetic construct
SEQUENCE: 21
ggagyatgtg gtttaattcg aagca                                             25

SEQ ID NO: 22          moltype = DNA  length = 20
FEATURE                Location/Qualifiers
source                 1..20
                       mol_type = other DNA
                       organism = synthetic construct
SEQUENCE: 22
agctgacgac aaccatgcac                                                   20

SEQ ID NO: 23          moltype = DNA  length = 22
FEATURE                Location/Qualifiers
source                 1..22
                       mol_type = other DNA
                       organism = synthetic construct
SEQUENCE: 23
aacgcgaaaa accttaccta cc                                                22

SEQ ID NO: 24          moltype = DNA  length = 22
FEATURE                Location/Qualifiers
source                 1..22
                       mol_type = other DNA
                       organism = synthetic construct
SEQUENCE: 24
tgccctttcg tagcaactag tg                                                22

SEQ ID NO: 25          moltype = DNA  length = 18
FEATURE                Location/Qualifiers
source                 1..18
                       mol_type = other DNA
                       organism = synthetic construct
SEQUENCE: 25
tgtagcggtg gaatgcgc                                                     18

SEQ ID NO: 26          moltype = DNA  length = 21
FEATURE                Location/Qualifiers
source                 1..21
                       mol_type = other DNA
                       organism = synthetic construct
SEQUENCE: 26
aattaagcca catgctccgc t                                                 21

SEQ ID NO: 27          moltype = DNA  length = 21
FEATURE                Location/Qualifiers
source                 1..21
                       mol_type = other DNA
                       organism = synthetic construct
SEQUENCE: 27
gctaacgcat taagtryccc g                                                 21

SEQ ID NO: 28          moltype = DNA  length = 18
FEATURE                Location/Qualifiers
source                 1..18
                       mol_type = other DNA
                       organism = synthetic construct
```

-continued

```
SEQUENCE: 28
gccatgcrgc acctgtct                                                18

SEQ ID NO: 29          moltype = DNA  length = 19
FEATURE                Location/Qualifiers
source                 1..19
                       mol_type = other DNA
                       organism = synthetic construct
SEQUENCE: 29
gcaactcttt acgcccagt                                               19

SEQ ID NO: 30          moltype = DNA  length = 18
FEATURE                Location/Qualifiers
source                 1..18
                       mol_type = other DNA
                       organism = synthetic construct
SEQUENCE: 30
gagaggatga tcagccag                                                18
```

METHOD OF TREATMENT WITH LACTIC ACID BACTERIA

CROSS-REFERENCE TO RELATED APPLICATIONS

This application is a continuation application of U.S. patent application Ser. No. 16/481,643, filed Jul. 29, 2019, which is a national phase application of PCT Application No. PCT/KR2018/001359, filed on Jan. 31, 2018, which claims the benefit and priority to Korean Patent Application No. 10-2017-0013632, filed on Jan. 31, 2017. The entire disclosures of the applications identified in this paragraph are incorporated herein by references.

TECHNICAL FIELD

The present invention relates to novel lactic acid bacteria, and more particularly, to novel lactic acid bacteria and various food and drug uses thereof, which may inhibit allergic reactions by means of various physiological activities such as an immunity regulatory effect, an inflammation reaction inhibiting effect, etc.

BACKGROUND

A hypersensitivity reaction refers to a reaction which does harm to a human body by causing an excessive immune reaction to a non-pathogen rather than bringing about an immune tolerance thereto in a human living body. The hypersensitivity reaction is roughly classified into four types according to its effect mechanism. A type 1 hypersensitivity reaction occurs in such a way that a specific antigen binds to Ig, which is mainly bound to an Fc receptor of a mast cell. Such reaction is also called an immediate hypersensitivity reaction because the reaction occurs right after being exposed to the antigen. The type 1 hypersensitivity reaction is generally caused by particulate antigens inhaled through breathing. As said particulate antigens, there are plant pollens, etc. As diseases or symptoms caused by the type 1 hypersensitivity reaction, there are acute hives, atopic dermatitis, allergic rhinitis, bronchial asthma, etc. A type 2 hypersensitivity reaction is caused by small molecules covalently binding to a surface component of human cells, and thus creating a modified structure, which an immune system recognizes as a heterogeneous material. In the type 2 hypersensitivity reaction, B cells produce IgG against a new epitope, after which the IgG binds to a modified cell, and thus causes a cell disruption through a complementary activity and phagocytosis. A type 3 hypersensitivity reaction is caused by soluble immune complexes, which are formed by means of binding between a soluble protein antigen and IgG, which is produced against the soluble protein antigen. In the type 3 hypersensitivity reaction, a part of the immune complexes is attached to a small wall of blood vessel or a pulmonary alveoli of lung, thus activating a complement, causing an inflammation reaction of damaging a tissue, and deteriorating a physiological function of the tissue. A type 4 hypersensitivity reaction is caused by products of an antigen-specific effector T cell, and is also called a delayed hypersensitivity reaction because it appears in one to three days after being exposed to the antigen.

The type 1 hypersensitivity reaction is an immediate reaction mediated by IgE. IgE antibodies are produced by plasma cells mainly present in mucous membranes of respiratory and digestive organs. Such produced IgE antibodies have a very high affinity with the surface receptors of mast cells and basophils, and thus mostly bind to those cells. It is a sensitized state in which most surface receptors of mast cells and basophils are bound to IgE antibodies. If being exposed to an allergen in the sensitized state, the allergen binds to the IgE antibody, thus causing a reaction between receptors, after which a granule in the mast cell fuses with a cell membrane, thus secreting chemical mediators such as histamine, cysteinyl leukotriene, prostaglandin and thromboxane. Such chemical mediators cause an early allergic reaction by increasing vascular permeability, enlarging blood vessels, contracting smooth muscles and accelerating secretory gland functions.

Allergic rhinitis, one of the diseases caused by said type 1 hypersensitivity reaction, refers to a symptomatic disorder, which leads to symptoms in the nose, eyes, ears, throat and the like by inducing an IgE-mediated inflammation after allergen exposure. Such allergic rhinitis is divided into intermittent AR or persistent AR based on a duration of symptoms according to the Allergic Rhinitis and Its Impact on Asthma Working Group, and is subdivided again into mild, moderate and severe. A prevalence rate of allergic rhinitis is generally about 10-30% in adults and about 40% in young children with a slight difference depending on reporters from country to country. The risk factors for allergic rhinitis are indoor and outdoor allergens, and the case in which a serum IgE level is 100 IU/ml or more before six years old. Allergic rhinitis may cause sinusitis, otitis media or conjunctivitis as a complication. If progressing chronically, such disease may aggravate asthma and sinusitis, and thus cause sleep disturbance, attention difficulty or maladjustment to social life. Asthma, one of the diseases caused by said type 1 hypersensitivity reaction, refers to a disease, in which symptoms such as respiratory distress, cough, wheezing sound, etc., occur repeatedly or spasmodically, and also refers to a representative allergic disease caused by a combination of genetic and environmental factors. In other words, such asthma occurs in such a way that an allergic constitution inherited from parents and surrounding asthma-inducing factors are involved in an interaction with each other, thus causing a disturbance to an immune system, and is mostly chronic and recurrent.

Various therapeutic methods have been studied to treat the allergic diseases caused by the type 1 hypersensitivity reaction. For example, anti-allergic drugs, histamine receptor antagonists (anti-histaminic agents), steroids, etc., have been used for treatment. However, it is known that all the followings have considerable side effects: anti-histaminic agents, which inhibit a signal transduction from peripheral nerves by competing with histamine for binding to histamine receptors; anti-allergic drugs, which attempt a reduction in symptoms by weakening an activity of cells producing chemical mediators; and steroids, which reduce inflammations by weakening immune responsiveness, most of which do not have a reliable therapeutic effect.

On the other hand, lactic acid bacteria are a product, which was obtained for the first time by Metchnikoff, who made an attempt at acidifying intestinal contents to prevent putrefactive organisms from growing and thus to achieve a therapeutic effect. In case of *Lactobacillus* genus thought to be a representative lactic acid bacterium, more than 165 species thereof have be found so far. As a live form of probiotic lactic acid bacteria, which have been used for treating allergic diseases, there is reportedly, for example, *Lactobacillus acidophilus* strain L-92 for allergic symptoms caused by Himalayan cedar pollens in Japan.

Numerous lactic acid bacteria, which are beneficial to a human body, reside in human digestive tracts, and there have been ongoing researches to apply the lactic acid bacteria isolated from the human digestive tracts to drug medicines or functional foods. In particular, the therapeutic agents for allergic diseases may need to be taken for a long period of time, and thus require such characteristics as an easy intake and high safety as well. The lactic acid bacteria belong to a group of candidates, which are very suitable for treatment of diseases as above and also satisfy the requirements for such treatment as well.

DETAILED DESCRIPTION OF THE INVENTION

Technical Problem

The present invention is applied against the conventional technological background, and an objective of the present invention is to provide novel lactic acid bacteria having an immunity regulatory effect and an inflammation reaction inhibiting effect.

Also, other objective of the present invention is to provide various food and drug uses of novel lactic acid bacteria.

Particularly, an objective of the present invention is to provide the novel lactic acid bacteria of *Bifidobacterium longum* IM55 or *Lactobacillus plantarum* IM76.

Other objective of the present invention is to provide a pharmaceutical composition for preventing or treating allergic diseases, containing *Bifidobacterium longum* IM55, *Lactobacillus plantarum* IM76 or mixtures thereof.

Another objective of the present invention is to provide a food composition for preventing or alleviating allergic diseases, containing *Bifidobacterium longum* IM55, *Lactobacillus plantarum* IM76 or mixtures thereof.

Still another objective of the present invention is to provide a pharmaceutical composition for preventing or treating immune diseases or inflammatory diseases, containing *Bifidobacterium longum* IM55, *Lactobacillus plantarum* IM76 or mixtures thereof.

Also, still another objective of the present invention is to provide a method for preventing or treating allergic diseases, including a step of administering *Bifidobacterium longum* IM55, *Lactobacillus plantarum* IM76 or mixtures thereof into an individual.

Further, still another objective of the present invention is to provide a use of *Bifidobacterium longum* IM55, *Lactobacillus plantarum* IM76 or mixtures thereof in preventing or treating allergic diseases.

Moreover, still another objective of the present invention is to provide a use of *Bifidobacterium longum* IM55, *Lactobacillus plantarum* IM76 or mixtures thereof in producing a drug for preventing or treating allergic diseases.

Furthermore, still another objective of the present invention is to provide a composition containing *Bifidobacterium longum* IM55 KCCM11961P, *Lactobacillus plantarum* IM76 KCCM11962P or mixtures thereof for a use in preventing or treating allergic diseases.

Technical Solution

In one aspect for achieving said objectives, the present invention provides *Bifidobacterium longum* IM55 (depository institution: the Korean Culture Center of Microorganisms (KCCM), date of deposit: Jan. 20, 2017, and accession number: KCCM11961P).

The *Bifidobacterium longum* IM55 of the present invention is characterized by being a novel lactic acid bacterium of *Bifidobacterium longum* isolated and identified from excrement of a human.

A 16S rDNA sequence for identification and classification of *Bifidobacterium longum* IM55 of the present invention is the same as SEQ ID NO: 1 attached to the present specification. Thus, the *Bifidobacterium longum* IM55 KCCM11961P of the present invention may include the 16S rDNA sequence of SEQ ID NO: 1.

As a result of analyzing said 16S rDNA sequence of SEQ ID NO: 1, such sequence was 99% homologous to that of known *Bifidobacterium longum* strains, thus showing the highest molecular phylogenetic relationship with *Bifidobacterium longum*. Thus, said lactic acid bacterium was identified as *Bifidobacterium longum*, then named as *Bifidobacterium longum* IM55, and then deposited to the KCCM on Jan. 20, 2017 (accession number: KCCM11961P).

In the present invention, said *Bifidobacterium longum* IM55 may use as a carbon source D-glucose, D-mannitol, D-lactose, D-sucrose, D-maltose, salicin, D-xylose, L-arabinose, esculin ferric citrate, D-raffinose and D-sorbitol.

In other aspect for achieving said objectives, the present invention provides *Lactobacillus plantarum* IM76 (depository institution: the Korean Culture Center of Microorganisms (KCCM), date of deposit: Jan. 20, 2017, and accession number: KCCM11962P).

The *Lactobacillus plantarum* IM76 of the present invention is characterized by being a novel lactic acid bacterium of *Lactobacillus plantarum* isolated and identified from kimchi, which is a traditional fermented food.

A 16S rDNA sequence for identification and classification of *Lactobacillus plantarum* IM76 of the present invention is the same as SEQ ID NO: 2 attached to the present specification. Thus, the *Lactobacillus plantarum* IM76 KCCM11962P of the present invention may include the 16S rDNA sequence of SEQ ID NO: 2.

As a result of analyzing said 16S rDNA sequence of SEQ ID NO: 2, such sequence was 99% homologous to that of known *Lactobacillus plantarum* strains, thus showing the highest molecular phylogenetic relationship with *Lactobacillus plantarum*. Thus, said lactic acid bacterium was identified as *Lactobacillus plantarum*, then named as *Lactobacillus plantarum* IM76, and then deposited to the KCCM on Jan. 20, 2017 (accession number: KCCM11962P).

In the present invention, said *Lactobacillus plantarum* IM76 may use as a carbon source L-arabinose, D-ribose, D-galactose, D-glucose, D-fructose, D-mannose, mannitol, sorbitol, N-acetyl-glucosamine, amygdaline, arbutin, esculin, salicin, cellobiose, maltose, lactose, melibiose, sucrose, trehalose, raffinose, gentiobiose, D-turanose and gluconate.

In another aspect for achieving said objectives, the present invention provides a pharmaceutical composition for preventing or treating allergic diseases, containing *Bifidobacterium longum* IM55 KCCM11961P, *Lactobacillus plantarum* IM76 KCCM11962P or mixtures thereof.

In the present invention, the term "allergic disease" means a disease, disorder or abnormal state, which is induced by causing hyperergia to a certain material of a human body, that is, by causing an excessive reaction of an immune system toward a material brought in from outside. Said material brought in from outside may be an allergen, i.e., an antigen which becomes a cause of the allergic disease. Said allergy may mean the hypersensitivity reaction caused in such a way that an inflammation mediator such as histamine is released by means of a material brought in from outside and thus leads to a disease, and said hypersensitivity reaction may be a type 1 hypersensitivity reaction, a type 2 hypersensitivity reaction, a type 3 hypersensitivity reaction or a type 4 hypersensitivity reaction. In the present invention, said allergic disease may be a disease caused by the IgE-mediated type 1 hypersensitivity reaction, and particularly may be selected from the group consisting of rhinitis, atopy, asthma, atopic dermatitis, allergic conjunctivitis, allergic otitis media, hives and anaphylactic shock. More particularly, said allergic disease in the present invention may be rhinitis, atopy or asthma.

In addition to an effect of controlling, preventing, alleviating and treating the allergic diseases above, a composition according to the present invention also shows an excellent effect on controlling, preventing, alleviating and treating the allergic diseases and complications thereof by normalizing the intestinal microorganisms modified by the allergic diseases.

The "*Bifidobacterium longum* IM55" of the present invention is the same as described above.

Particularly, the *Bifidobacterium longum* IM55 contained in the pharmaceutical composition of the present invention may be a live cell body thereof, a dead cell body thereof, a culture product thereof, a crushed product thereof or an extract thereof, but any form of *Bifidobacterium longum* IM55 may be used without limitation, as long as it may achieve a preventive or therapeutic effect on the allergic diseases.

The "*Lactobacillus plantarum* IM76" of the present invention is the same as described above.

Particularly, the *Lactobacillus plantarum* IM76 contained in the pharmaceutical composition of the present invention may be a live cell body thereof, a dead cell body thereof, a culture product thereof, a crushed product thereof or an extract thereof, but any form of *Lactobacillus plantarum* IM76 may be used without limitation, as long as it may achieve a preventive or therapeutic effect on the allergic diseases.

In the present invention, a mixture of *Bifidobacterium longum* IM55 and *Lactobacillus plantarum* IM76 may be mixed in a range capable of achieving an effect of preventing or treating the allergic diseases, and said mixture ratio may be 10:1 to 1:10, but not limited thereto. Particularly, a ratio of *Bifidobacterium longum* IM55 and *Lactobacillus plantarum* IM76 may be 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or 1:10. A mixture thereof shows a remarkable effect of preventing or treating allergic diseases through a synergy effect according to mixing between such lactic acid bacteria.

In the present invention, the term "live cell body" means a novel lactic acid bacterium itself of the present invention; "dead cell body" means a lactic acid bacterium, which is sterilized by means of heating, pressurization, drug treatment or the like; and "crushed product" means a lactic acid bacterium, which is crushed by means of enzymatic treatment, homogenization, ultrasonic treatment or the like. Also, in the present invention, the term "extract" means a product obtained by carrying out an extraction for lactic acid bacteria with a known extraction solvent.

In the present invention, the term "culture product" means a product obtained by culturing lactic acid bacteria in a known medium, and said product may include novel lactic acid bacteria. Said medium may be selected from a known liquid medium or solid medium, and may be, for example, an MRS liquid medium, a GAM liquid medium, an MRS agar medium, a GAM agar medium or a BL agar medium, but not limited thereto.

Also, in the present invention, the term "prevention" means all the acts, which inhibit a symptom of allergic diseases or delay a progress thereof by administering the pharmaceutical composition of the present invention.

Also, in the present invention, the term "treatment" means all the acts, which improve or beneficially change a symptom of the allergic diseases by administering the pharmaceutical composition of the present invention.

A content of novel lactic acid bacteria, etc., which are an effective component of the pharmaceutical composition of the present invention, may be adjusted within various ranges depending on a specific form of the composition and a purpose or aspect of use thereof. In the pharmaceutical composition according to the present invention, the content of the effective component is not greatly limited, and may be, for example, 0.01 to 99 wt %, particularly 0.1 to 75 wt %, and more particularly 0.5 to 50 wt % based on the total weight of the composition.

The pharmaceutical composition of the present invention may further contain at least one known effective component having an immunity regulatory effect, an inflammation reaction inhibiting effect and an effect of preventing or treating allergic diseases (for example, asthma, rhinitis, atopic dermatitis, etc.).

Particularly, the pharmaceutical composition of the present invention may further contain at least one selected from the group including chitosan, inulin and citrus pectin.

Said chitosan, inulin, citrus pectin or mixtures of at least two thereof is contained in the pharmaceutical composition of the present invention, and thus may act as prebiotics when novel lactic acid bacteria achieve an effect of preventing and treating allergic diseases.

Also, the pharmaceutical composition according to the present invention may further contain additives like pharmaceutically acceptable carriers in addition to novel lactic acid bacteria, which are an effective component. The carrier, which may be contained in the pharmaceutical composition of the present invention, includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil and the like, but not limited thereto.

The pharmaceutical composition of the present invention may be formulated into a dosage form for oral administration or a dosage form for parenteral administration by means of a conventional method, and may be compounded by using diluents or excipients such as fillers, extenders, binders, humectants, disintegrants, surfactants, etc., which are generally used for being formulated into a preparation.

If being formulated into a solid preparation for oral administration, the pharmaceutical composition of the present invention may include tablet, pill, powder, granule, capsule preparations, etc., and such solid preparation may contain at least one excipient, for example, starch, calcium carbonate, sucrose, lactose, gelatin or the like in its effective component. Also, in addition to simple excipients, the solid preparation may contain lubricants, etc., such as magnesium stearate and talc, but not limited thereto.

If being formulated into a liquid preparation for oral administration, the pharmaceutical composition of the present invention may include suspending agents, liquid for internal use, emulsion, syrup and the like, and may also contain various excipients, for example, humectants, sweetening agents, flavoring agents, preservatives, etc. in addition to water and liquid paraffin, which are frequently used simple diluents, but not limited thereto.

If being formulated into a preparation for parenteral administration, the pharmaceutical composition of the present invention may include sterilized aqueous solution, non-aqueous solvent, suspending agents, emulsion, freeze-dried preparations or suppositories. As the non-aqueous solvent and the suspending solvent, the followings may be included, but not limited thereto: propylene glycol, polyethylene glycol, vegetable oil like olive oil, injectable ester like ethyl oleate, etc. As a base of the suppositories, the followings may be used: witepsol, macrogol, tween 61, cacao butter, laurinum, glycerogelatin, etc.

The pharmaceutical composition of the present invention may be orally or parenterally administered into mammals including humans according to an intended method. As the parenteral administration method, there are an external use on skin, intraperitoneal injection, rectal injection, subcutaneous injection, intravenous injection, intramuscular injection, intrathoracic injection methods, or the like. As long as it is a pharmaceutically effective amount, a dosage of the pharmaceutical composition of the present invention is not greatly limited, and a range thereof varies depending on a patient's weight, age, gender, health condition, diet, administration time, administration method, excretion rate and severity of a disease. A conventional daily dosage of the pharmaceutical composition of the present invention is not greatly limited, but may be particularly 0.1 to 3000 mg/kg and more particularly 0.5 to 2000 mg/kg based on the effective component, and may be administered once a day or divided into several times a day.

Said "pharmaceutically effective amount" means an amount enough to treat a disease at a reasonable benefit/risk ratio applicable to medical treatment, and may be determined according to factors including an individual's disease type, severity, activity of a drug, sensitivity to the drug, an administration time, an administration route, an excretion rate, a treatment period and a concurrently used drug, as well as other factors well known in a pharmaceutical field.

Said "administration" means providing a predetermined pharmaceutical composition of the present invention to an individual by means of any appropriate method. At this time, the individual refers to animals, and may be typically mammals, on which treatment using the novel lactic acid bacteria of the present invention may show a beneficial effect. A preferable example of such individual may include primates like humans. Also, such individual may include all the individuals having a symptom of allergic diseases, or having a risk of having such symptom.

Further, in another aspect for achieving said objectives, the present invention provides a food composition for preventing or alleviating allergic diseases, containing *Bifidobacterium longum* IM55 KCCM11961P, *Lactobacillus plantarum* IM76 KCCM11962P or mixtures thereof.

In the present invention, the terms "*Bifidobacterium longum* IM55," "*Lactobacillus plantarum* IM76," "allergic disease" and the like are the same as described above.

The food composition of the present invention may be used as a health functional food. Said "health functional food" means a food prepared and processed by using a raw material or component, which has functionality useful for a human body according to the Health Functional Food Acts, and the "functionality" means taking such food for the purpose of adjusting nutrients with regard to structures and functions of the human body or obtaining an effect valuable for health uses such as a physiological action, etc.

The food composition of the present invention may contain conventional food additives, and whether a certain item is suitable as said "food additives" or not is decided on the basis of specifications and standards on such item according to the general rules, other general testing methods and the like of the Food Additives Code approved by the Ministry of Food and Drug Safety, unless there are other regulations.

As items listed on said "Food Additives Code," there may be, for example, chemical compounds such as ketones, glycine, potassium citrate, nicotinic acid, cinnamic acid, etc.; natural additives such as persimmon color, licorice extract, crystalline cellulose, kaoliang color, guar gum, etc.; and mixed formulations such as L-sodium glutamate formulation, alkali additives for noodles, preservatives formulation, tar color formulation, etc.

The food composition of the present invention may contain *Bifidobacterium longum* IM55, *Lactobacillus plantarum* IM76 or mixtures thereof in an amount of 0.01 to 99 wt %, particularly 0.1 to 75 wt %, and more particularly 0.5 to 50 wt % with regard to the total weight of the composition.

Also, the food composition of the present invention may be prepared and processed in a form of tablet, capsule, powder, granule, liquid, pill, etc., for the purpose of preventing and/or alleviating allergic diseases.

For example, the food composition in said form of tablet may be prepared by granulating *Bifidobacterium longum* IM55, *Lactobacillus plantarum* IM76 or mixtures thereof, and mixtures of excipients, binders, disintegrants and other additives by means of a conventional method; then by putting glidants, etc. thereinto; and then by carrying out compression molding, or may be prepared by directly putting said mixtures into compression molding. Also, the health functional food in said form of tablet may contain corrigent, etc., if needed, and may be coated with an appropriate coating agent, if needed.

Out of the food compositions in the form of capsule, a hard capsule preparation may be prepared by filling *Bifidobacterium longum* IM55, *Lactobacillus plantarum* IM76 or mixtures thereof; and mixtures of additives such as excipients, etc.; or granules or coated granules thereof into a conventional hard capsule, and a soft capsule preparation may be prepared by filling *Bifidobacterium longum* IM55, *Lactobacillus plantarum* IM76 or mixtures thereof; and mixtures of additives such as excipients, etc. into a capsule base with gelatin, etc. Said soft capsule preparation may contain plasticizers, coloring agents, preservatives, etc., such as glycerin, sorbitol or the like, if needed.

The food composition in the form of pill may be compounded by molding *Bifidobacterium longum* IM55, *Lactobacillus plantarum* IM76 or mixtures thereof, and mixtures of excipients, binders, disintegrants, etc. by means of an appropriate method, and may be coated with white sugar or other appropriate coating agents, or may be covered with a pill-coating agent by means of starch, talc or appropriate materials, if needed.

The food composition in the form of granule may be prepared into a granular form with *Bifidobacterium longum* IM55, *Lactobacillus plantarum* IM76 or mixtures thereof, and mixtures of excipients, binders, disintegrants, etc., by means of an appropriate method, and may contain flavoring agents, corrigent, etc., if needed. When carrying out a following granularity test on the health functional food in the form of granule with no. 12 (1680 μm), no. 14 (1410 μm) and no. 45 (350 μm) sieves, the entire amount passes through the no. 12 sieve, 5% or less of the total amount remain on the no. 14 sieve, and 15.0% or less of the total amount may pass through the no. 45 sieve.

The definition of terms such as said excipients, binders, disintegrants, glidants, corrigent, flavoring agents, etc., includes those having functions the same as or similar to those described in documents known in the art (an explanatory edition of the Korean Pharmacopoeia, Munseong Publishing, the Korean Association of Colleges of Pharmacy, the 5th revised edition, p33-48, 1989).

A type of said food is not particularly limited. As an example of food, to which an extract of the present invention may be added, there are beverages, chewing gums, vitamin complexes, drinks, etc., including food compositions in a conventional sense, in particular, health functional foods all.

Furthermore, in another aspect for achieving said objectives, the present invention provides a pharmaceutical composition for preventing or treating immune diseases or inflammatory diseases, containing *Bifidobacterium longum* IM55 KCCM11961P, *Lactobacillus plantarum* IM76 KCCM11962P or mixtures thereof.

In the present invention, the terms related to the pharmaceutical composition, including "*Bifidobacterium longum* IM55" and "*Lactobacillus plantarum* IM76" are the same as described above.

In the present invention, the term "immune disease" means a disease, which becomes problematic upon the occurrence of a certain immune reaction, and particularly may be an autoimmune disease, transplant rejection or graft-versus-host disease, but not limited thereto. The autoimmune disease may be Crohn's disease, erythema, rheumatoid arthritis, Hashimoto's thyroiditis, pernicious anemia, Addison's disease, type 1 diabetes, lupus, chronic fatigue syndrome, fibromyalgia syndrome, hypothyroidism and hyperthyroidism, scleroderma, Behcet's disease, inflammatory bowel disease, multiple sclerosis, myasthenia gravis, Meniere's syndrome, Guillain-Barre syndrome, Sjogren's syndrome, leukoplakia, endometriosis, psoriasis, leukoplakia, systemic scleroderma, asthma, ulcerative colitis or the like.

In the present invention, the term "inflammatory disease" collectively means diseases, of which main lesion is inflammations. The inflammatory disease of the present invention may be at least one selected from the group including arthritis, gout, hepatitis, obesity, corneitis, gastritis, enteritis, nephritis, colitis, diabetes, tuberculosis, bronchitis, pleurisy, peritonitis, spondylitis, pancreatitis, inflammatory pain, urethritis, cystitis, vaginitis, arteriosclerosis, septicemia, burn, dermatitis, periodontitis and gingivitis. Particularly, said inflammatory disease may be colitis.

In addition to an effect of controlling, preventing, alleviating and treating the inflammatory diseases above, the composition according to the present invention also shows an excellent effect on controlling, preventing, alleviating and treating inflammatory diseases and complications thereof by normalizing the intestinal microorganisms, which are modified by the inflammatory diseases.

Moreover, in another aspect for achieving said objectives, the present invention provides a food composition for preventing or alleviating immune diseases or inflammatory diseases, containing *Bifidobacterium longum* IM55 KCCM11961P, *Lactobacillus plantarum* IM76 KCCM11962P or mixtures thereof.

In the present invention, the terms related to the food composition, including "*Bifidobacterium longum* IM55" and "*Lactobacillus plantarum* IM76" are the same as described above.

Besides, in another aspect for achieving said objectives, the present invention provides a method for preventing or treating allergic diseases, including a step of administering *Bifidobacterium longum* IM55 KCCM1961P, *Lactobacillus plantarum* IM76 KCCM11962P or mixtures thereof into an individual.

In the present invention, the terms such as "*Bifidobacterium longum* IM55," "*Lactobacillus plantarum* IM76," "administration," "individual," "allergic disease" and the like are the same as described above.

In addition, in another aspect for achieving said objectives, the present invention provides a use of *Bifidobacterium longum* IM55 KCCM11961P, *Lactobacillus plantarum* IM76 KCCM11962P or mixtures thereof in preventing or treating allergic diseases.

Also, in another aspect for achieving said objectives, the present invention provides a use of *Bifidobacterium longum* IM55 KCCM11961P, *Lactobacillus plantarum* IM76 KCCM11962P or mixtures thereof in producing a drug for preventing or treating allergic diseases.

Further, in another aspect for achieving said objectives, the present invention provides a composition containing *Bifidobacterium longum* IM55 KCCM11961P, *Lactobacillus plantarum* IM76 KCCM11962P or mixtures thereof for a use in preventing or treating allergic diseases.

Furthermore, in another aspect for achieving said objectives, the present invention provides a method for preventing or treating immune diseases or inflammatory diseases, including a step of administering *Bifidobacterium longum* IM55 KCCM11961P, *Lactobacillus plantarum* IM76 KCCM11962P or mixtures thereof into an individual.

In the present invention, the terms such as "*Bifidobacterium longum* IM55," "*Lactobacillus plantarum* IM76," "administration," "individual," "immune disease," "inflammatory disease" and the like are the same as described above.

Moreover, in another aspect for achieving said objectives, the present invention provides a use of *Bifidobacterium longum* IM55 KCCM11961P, *Lactobacillus plantarum* IM76 KCCM11962P or mixtures thereof in preventing or treating immune diseases or inflammatory diseases.

Besides, in another aspect for achieving said objectives, the present invention provides a use of *Bifidobacterium longum* IM55 KCCM11961P, *Lactobacillus plantarum* IM76 KCCM11962P or mixtures thereof in producing a drug for preventing or treating immune diseases or inflammatory diseases.

In addition, in another aspect for achieving said objectives, the present invention provides a composition containing *Bifidobacterium longum* IM55 KCCM11961P, *Lactobacillus plantarum* IM76 KCCM11962P or mixtures thereof for a use in preventing or treating immune diseases or inflammatory diseases.

Advantageous Effects

*Bifidobacterium longum* IM55 or *Lactobacillus plantarum* IM76 according to the present invention is safe without toxicity in a human body; has excellent physiological activities such as an immunity regulatory effect and an inflammation reaction inhibiting effect; and has an effect of normalizing intestinal microorganisms. Thus, *Bifidobacterium longum* IM55, *Lactobacillus plantarum* IM76 or mixtures thereof may be used as a material for preventing, alleviating or treating not only allergic diseases but also immune diseases and inflammatory diseases.

Figure 2:
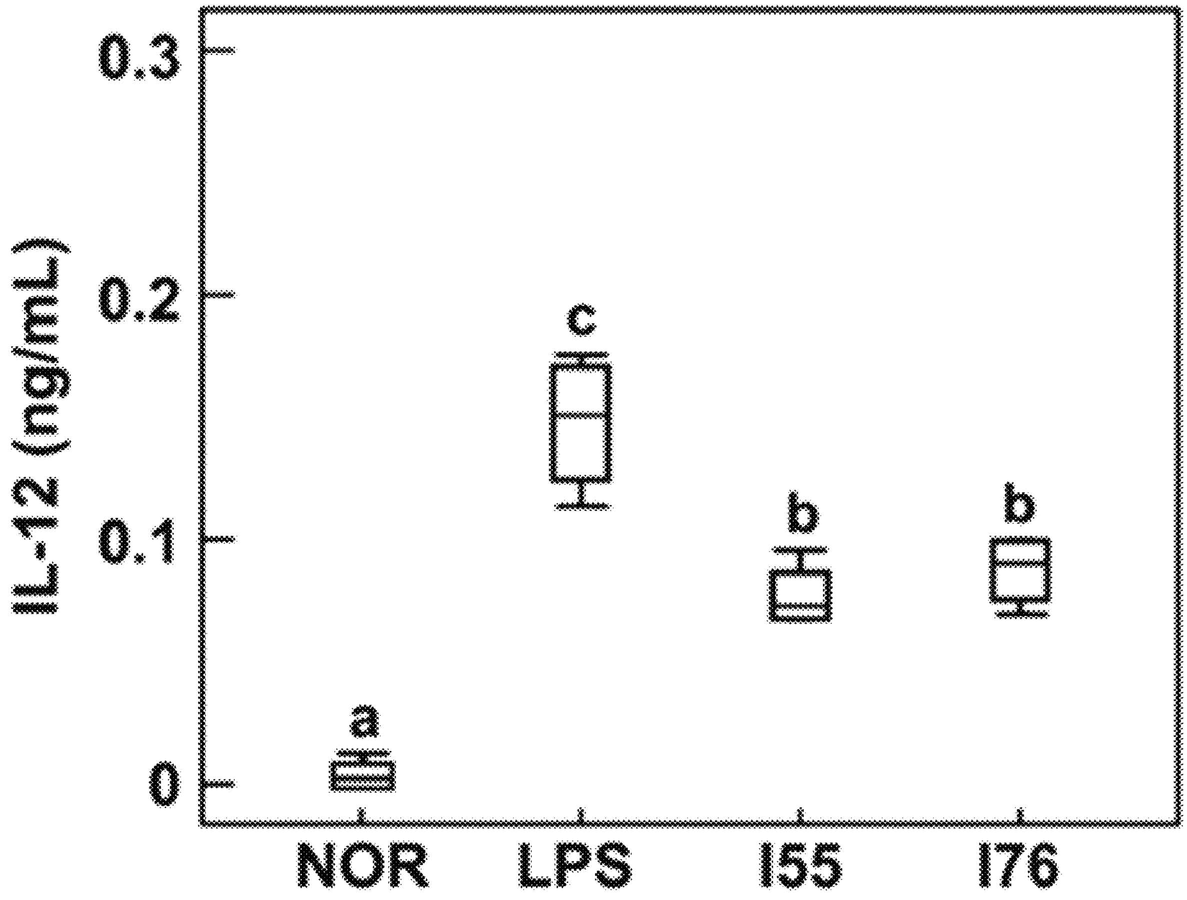

FIG. 2 is a graph of identifying that a concentration of IL-12 is decreased upon treating macrophage with *Bifidobacterium longum* IM55 or *Lactobacillus plantarum* IM76.

Figure 3:
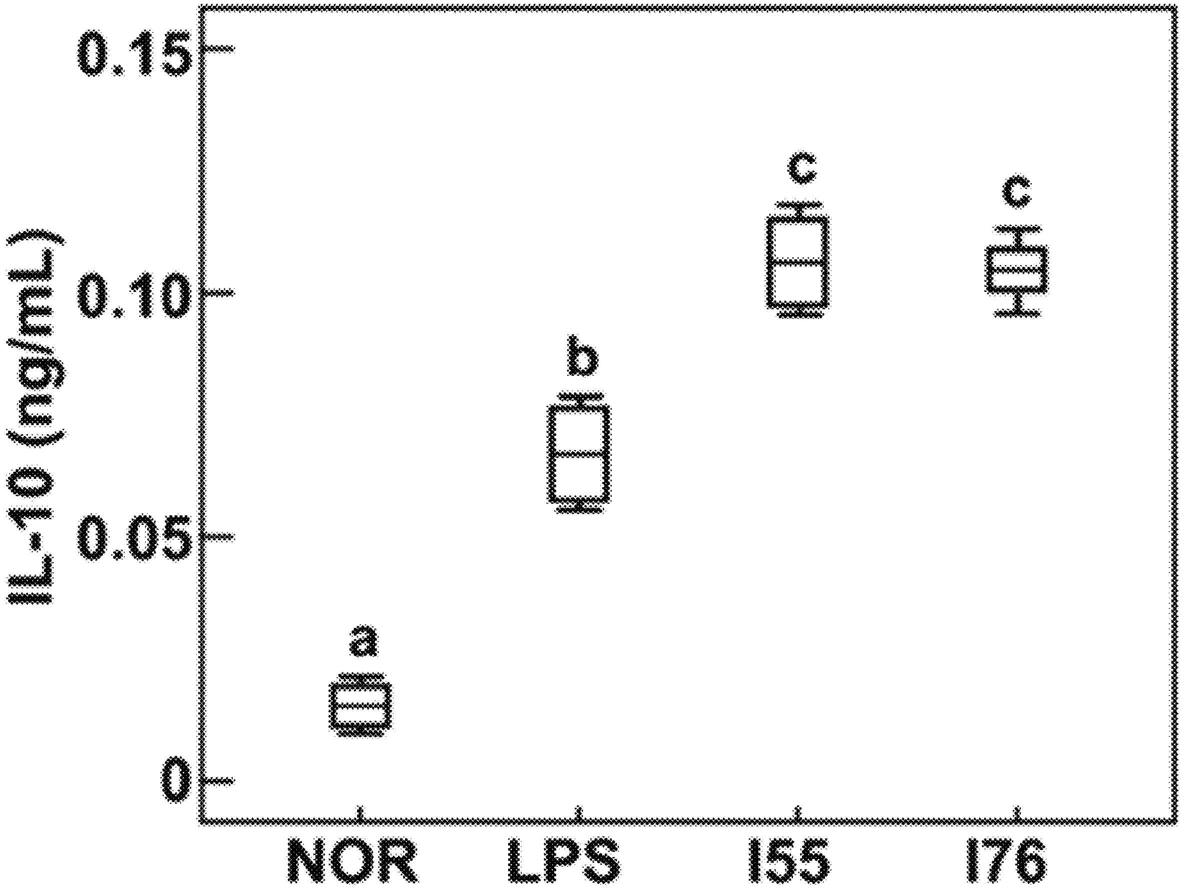

FIG. 3 is a graph of identifying that a concentration of IL-10 is increased upon treating dendritic cells with *Bifidobacterium longum* IM55 or *Lactobacillus plantarum* IM76.

Figure 4:
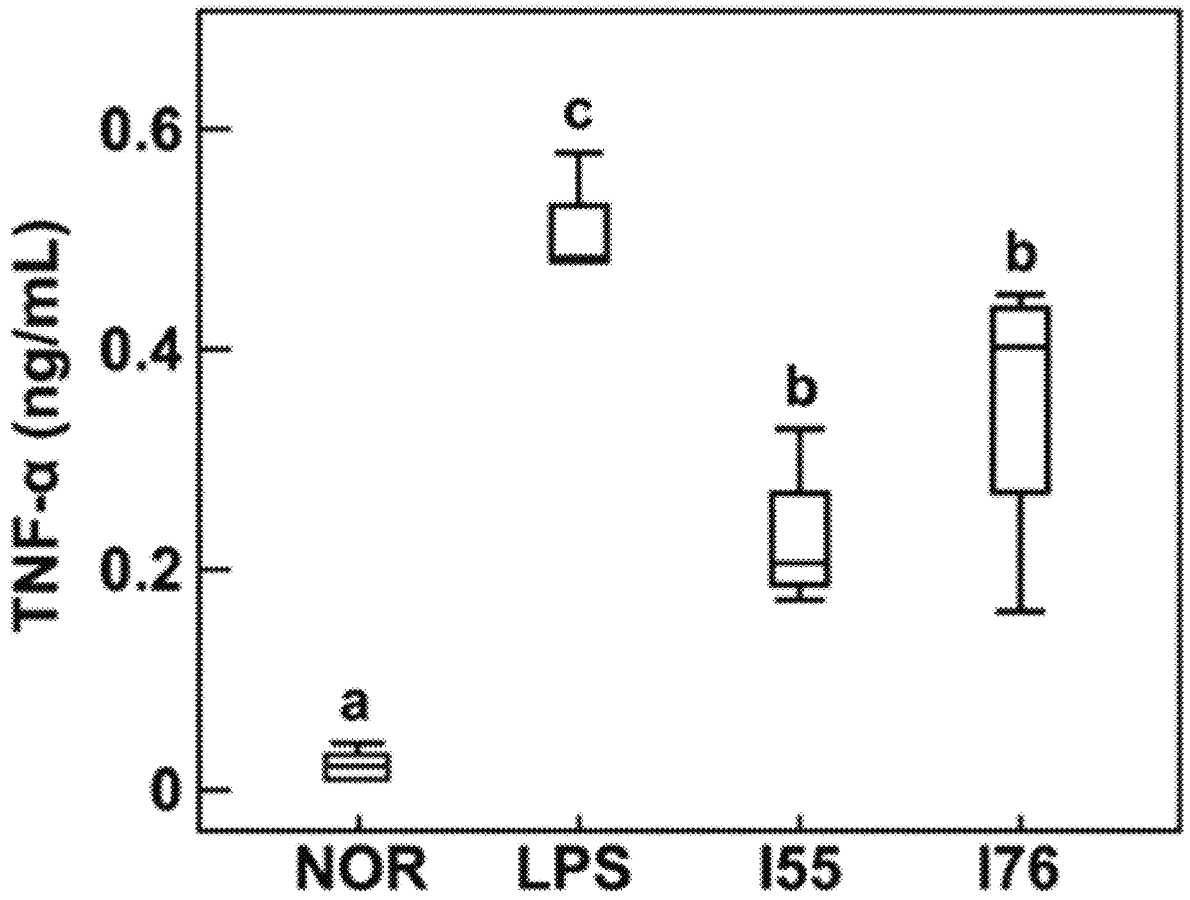

FIG. 4 is a graph of identifying that a concentration of TNF-α is decreased upon treating dendritic cells with *Bifidobacterium longum* IM55 or *Lactobacillus plantarum* IM76.

Figure 5:
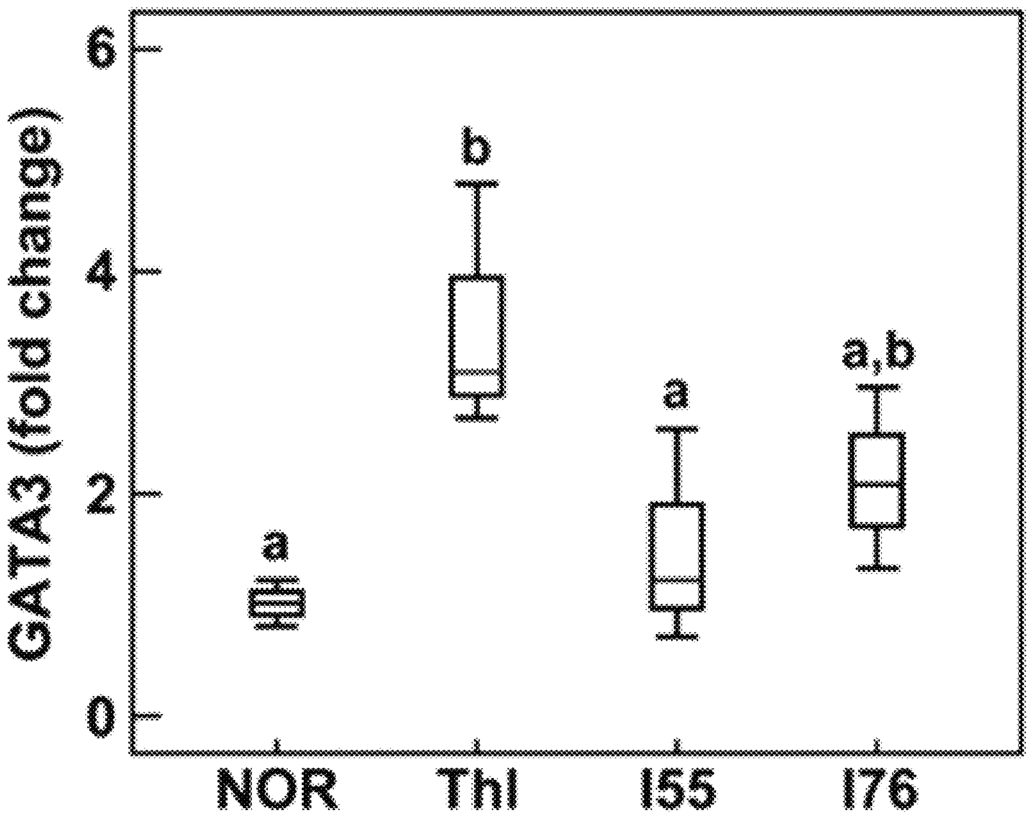

FIG. 5 is a graph of identifying that an expression level of GATA3 is inhibited as a result of treatment with *Bifidobacterium longum* IM55 or *Lactobacillus plantarum* IM76 upon inducing a differentiation of T cells into Th2 cells (NOR, a normal control group; Th1, a group dosed with a Th2 cytodifferentiation inducer; 155, a group with induced Th2 cytodifferentiation+dosed with *Bifidobacterium longum* IM55 at $1\times10^5$ CFU/ml; and 176, a group with induced Th2 cytodifferentiation+dosed with *Lactobacillus plantarum* IM76 at $1\times10^5$ CFU/ml are hereinafter the same as in FIG. 6).

Figure 6:
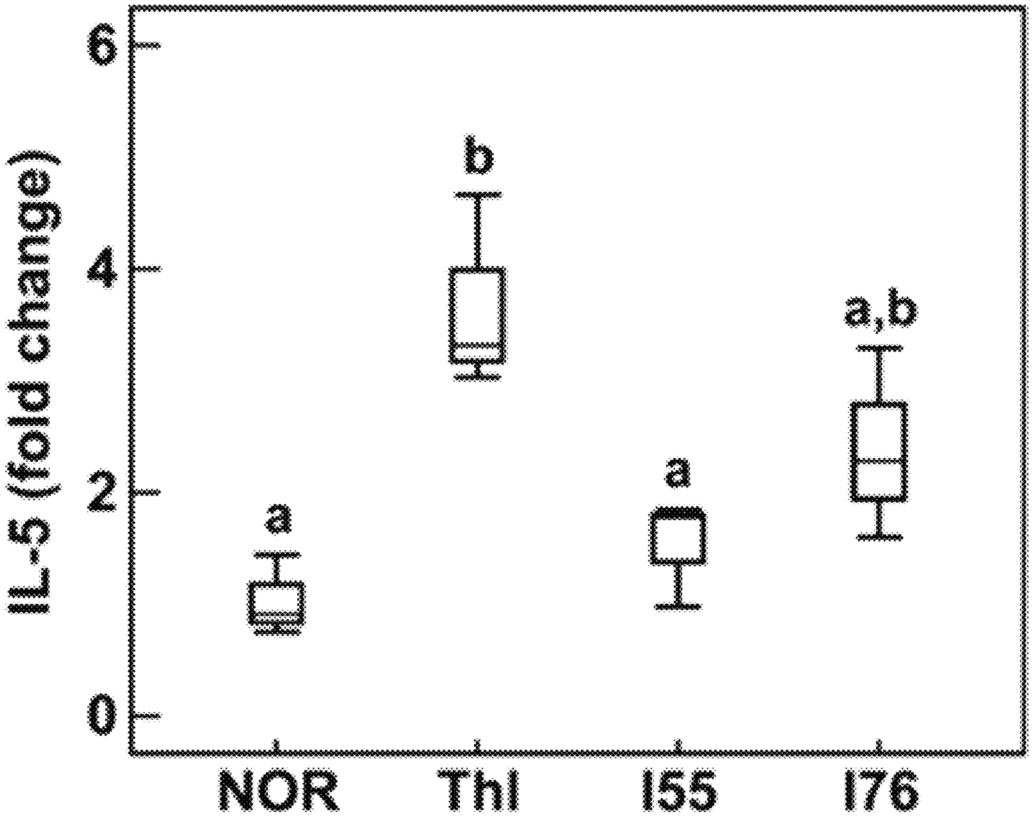

FIG. 6 is a graph of identifying that an expression level of IL-5 is inhibited as a result of treatment with *Bifidobacterium longum* IM55 or *Lactobacillus plantarum* IM76 upon inducing a differentiation of T cells into Th2 cells.

Figure 7:
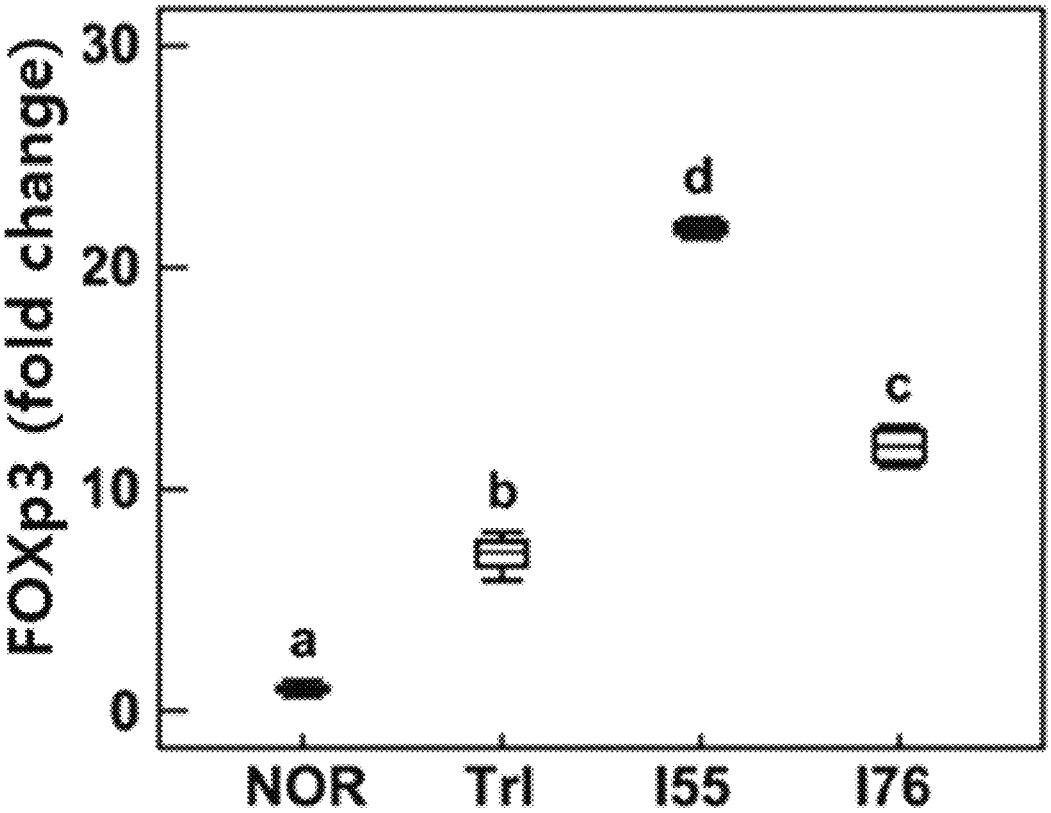

FIG. 7 is a graph of identifying that an expression level of FOXp3 is increased as a result of treatment with *Bifidobacterium longum* IM55 or *Lactobacillus plantarum* IM76 upon inducing a differentiation of T cells into Treg cells (NOR, a normal control group; TrI, a group dosed with a Treg cytodifferentiation inducer; I55, a group with induced Treg cytodifferentiation+dosed with *Bifidobacterium longum* IM55 at $1\times10^5$ CFU/ml; and 176, a group with induced Treg cytodifferentiation+dosed with *Lactobacillus plantarum* IM76 at $1\times10^5$ CFU/ml are hereinafter the same as in FIG. 8).

Figure 8:
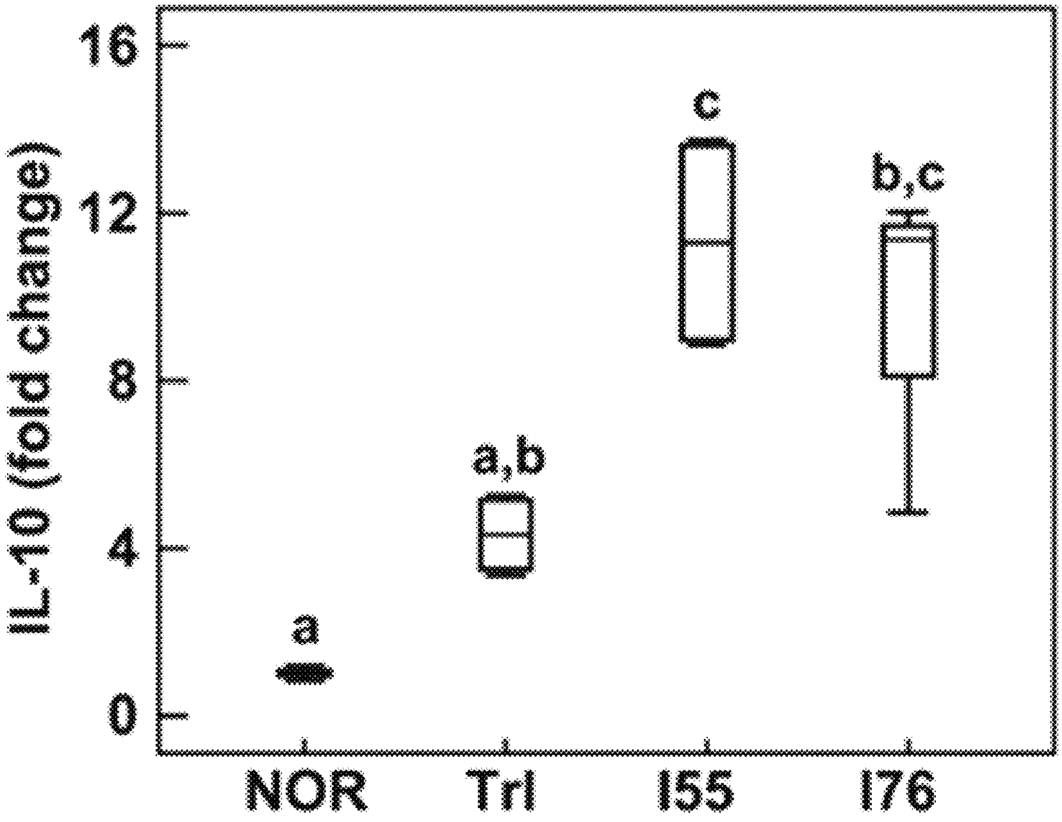

FIG. 8 is a graph of identifying that an expression level of IL-10 is increased as a result of treatment with *Bifidobacterium longum* IM55 or *Lactobacillus plantarum* IM76 upon inducing a differentiation of T cells into Treg cells.

Figure 9:
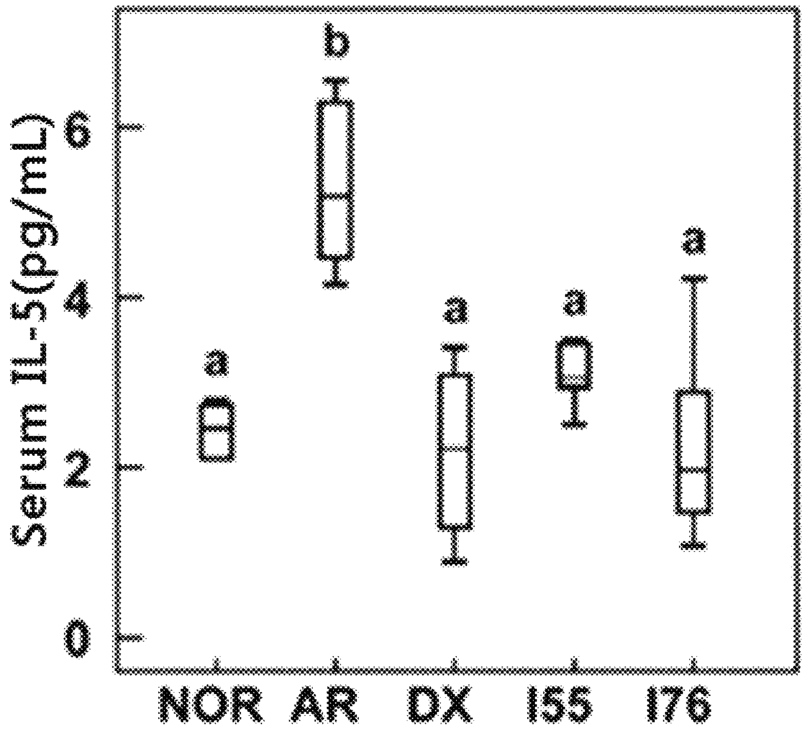

FIG. 9 is a graph of identifying that a serum concentration of IL-5 is decreased upon administering *Bifidobacterium longum* IM55 or *Lactobacillus plantarum* IM76 into an animal model with induced allergic rhinitis and asthma (NOR, a normal control group (orally administered with PBS only); CON or AR, a group with an induced disease; DX, a group with an induced disease+intraperitoneally dosed with dexamethasone at 1 mg/kg b.w.; 155, a group with an induced disease+orally dosed with *Bifidobacterium longum* IM55 at $1\times10^9$ CFU/mouse; and 176, a group with an induced disease+orally dosed with *Lactobacillus plantarum* IM76 at $1\times10^9$ CFU/mouse are hereinafter the same as in FIGS. 10 to 17).

Figure 10:
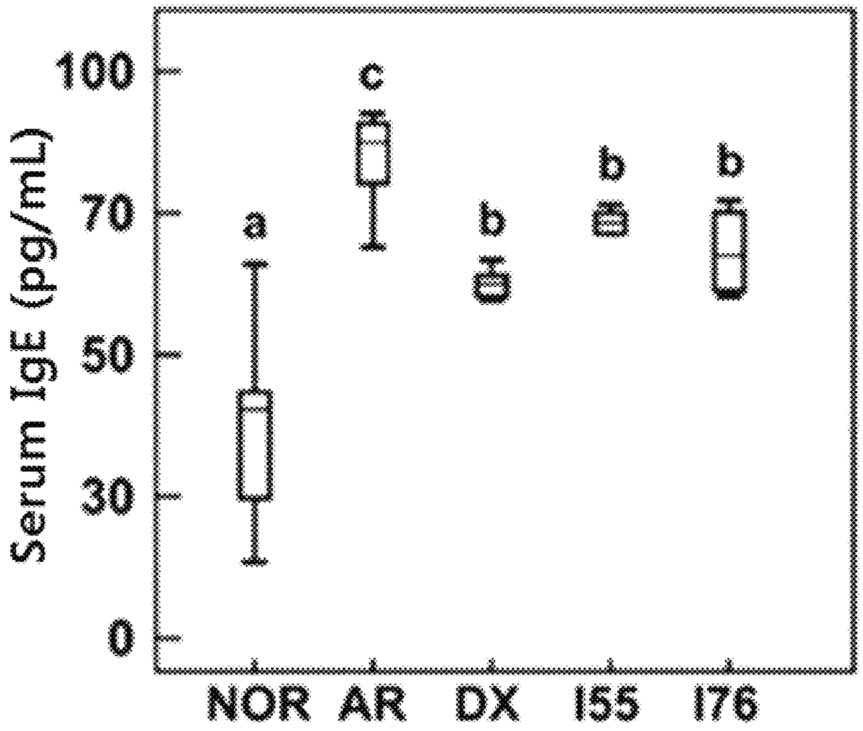

FIG. 10 is a graph of identifying that a serum concentration of IgE is decreased upon administering *Bifidobacterium longum* IM55 or *Lactobacillus plantarum* IM76 into an animal model with induced allergic rhinitis and asthma.

Figure 11:
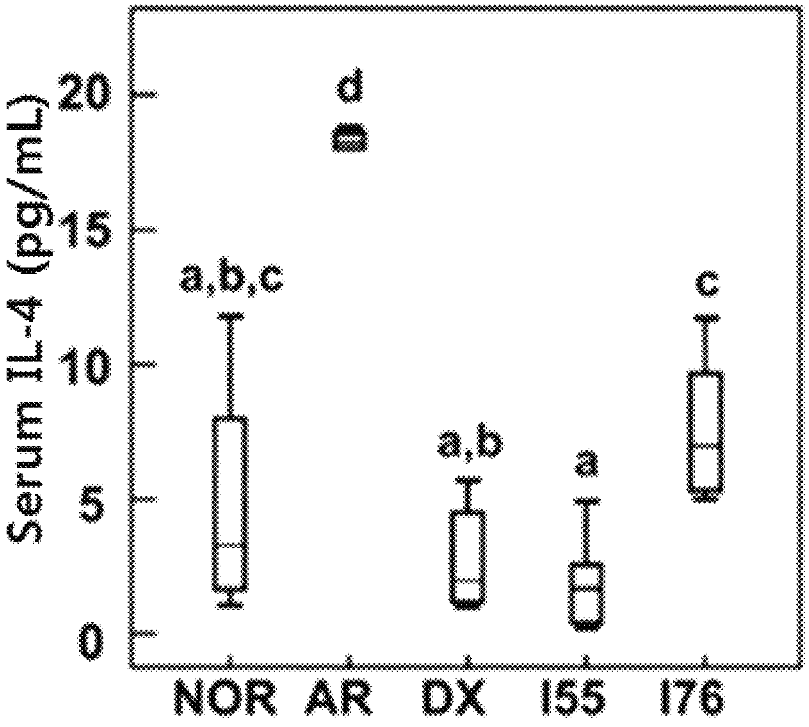

FIG. 11 is a graph of identifying that a serum concentration of IL-4 is decreased upon administering *Bifidobacterium longum* IM55 or *Lactobacillus plantarum* IM76 into an animal model with induced allergic rhinitis and asthma.

Figure 12:
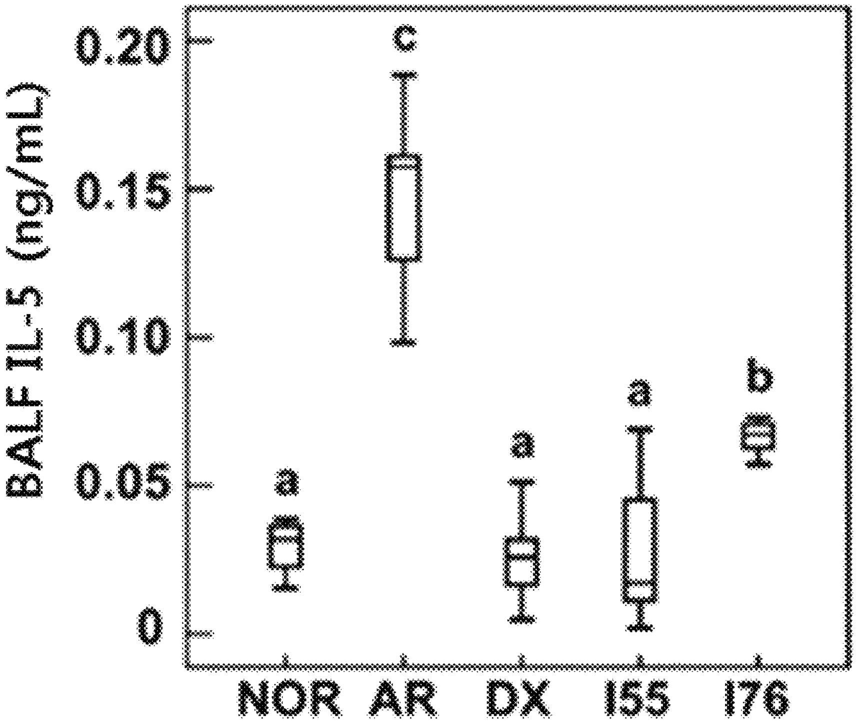

FIG. 12 is a graph of identifying that a concentration of IL-5 in bronchoalveolar lavage fluid (BALF) is decreased upon administering *Bifidobacterium longum* IM55 or *Lactobacillus plantarum* IM76 into an animal model with induced allergic rhinitis and asthma.

Figure 13:
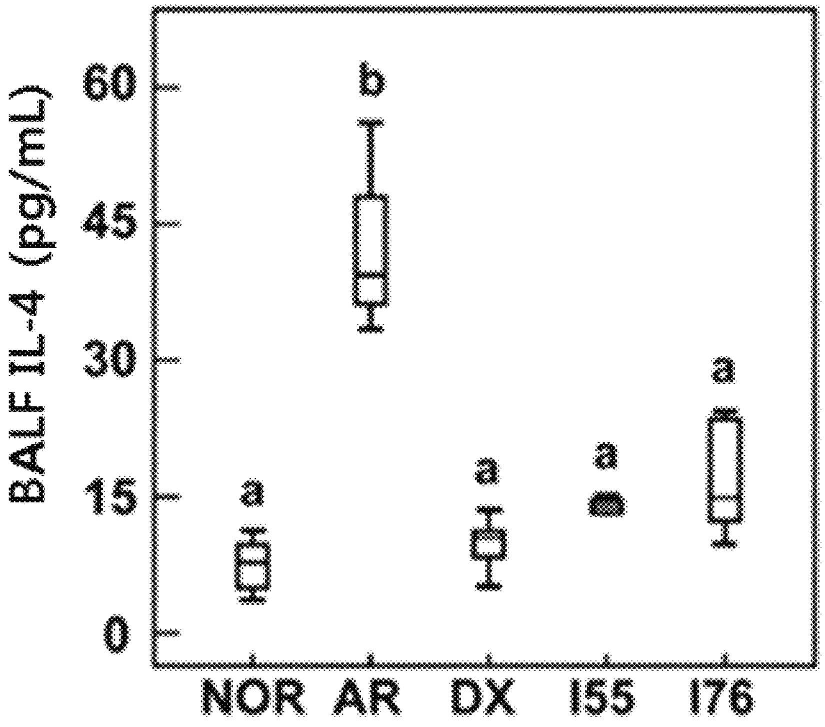

FIG. 13 is a graph of identifying that a concentration of IL-4 in the BALF is decreased upon administering *Bifidobacterium longum* IM55 or *Lactobacillus plantarum* IM76 into an animal model with induced allergic rhinitis and asthma.

Figure 14:
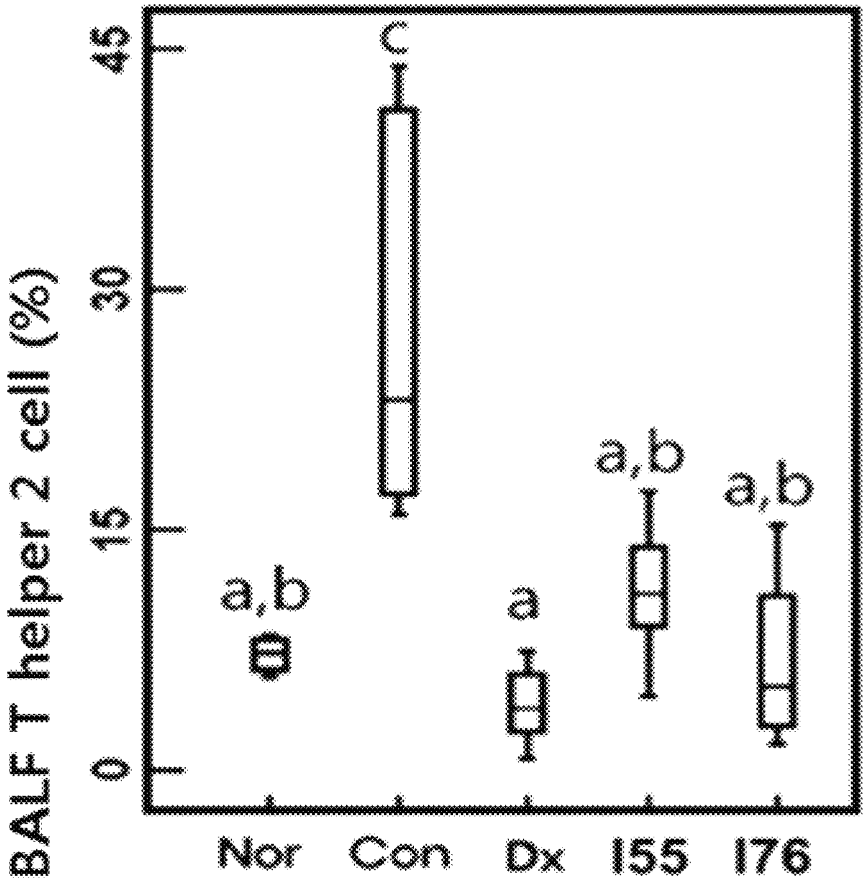

FIG. 14 is a graph of identifying that a distribution rate of Th2 cells in the BALF is decreased upon administering *Bifidobacterium longum* IM55 or *Lactobacillus plantarum* IM76 into an animal model with induced allergic rhinitis and asthma.

Figure 15:
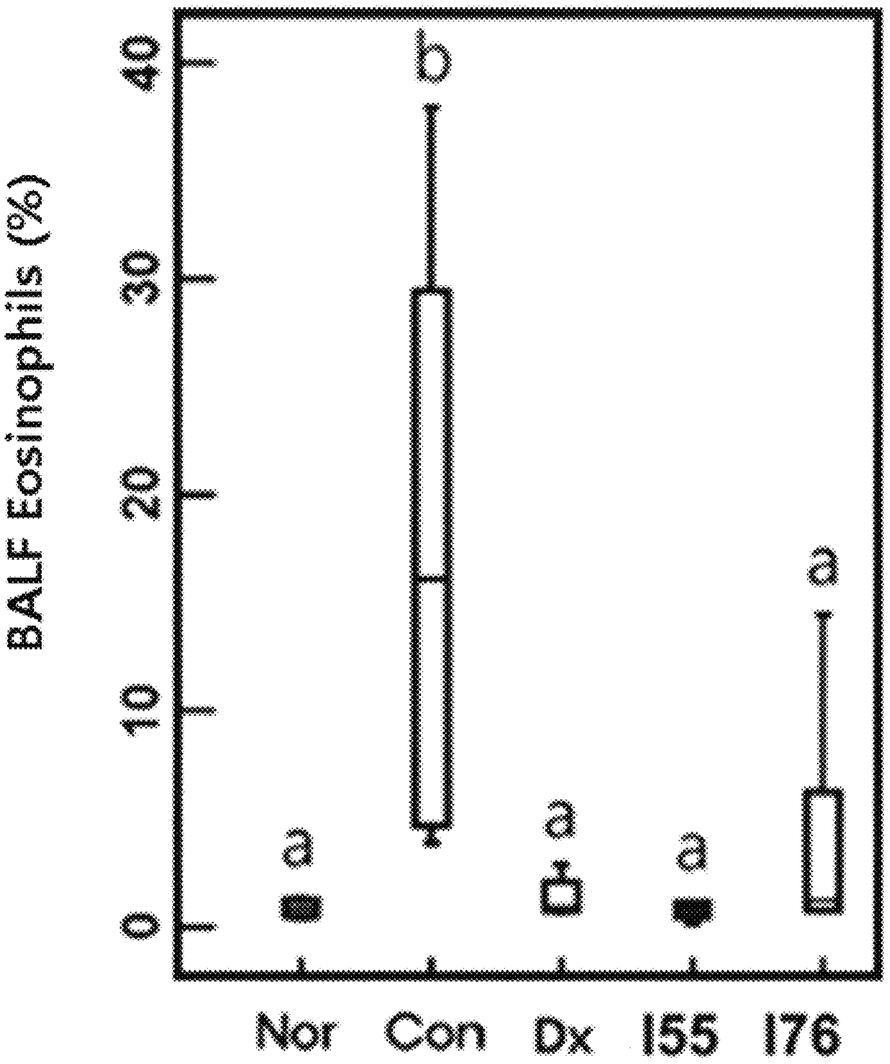

FIG. 15 is a graph of identifying that a distribution rate of eosinophil cells in the BALF is decreased upon administering *Bifidobacterium longum* IM55 or *Lactobacillus plantarum* IM76 into an animal model with induced allergic rhinitis and asthma.

Figure 16:
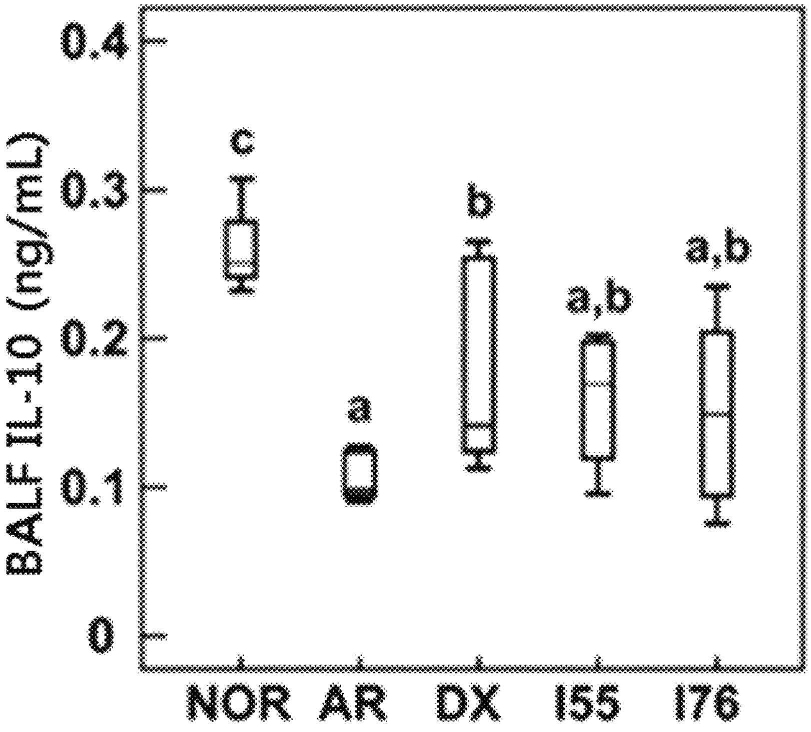

FIG. 16 is a graph of identifying that a concentration of IL-10 in the BALF is increased upon administering *Bifidobacterium longum* IM55 or *Lactobacillus plantarum* IM76 into an animal model with induced allergic rhinitis and asthma.

Figure 17:
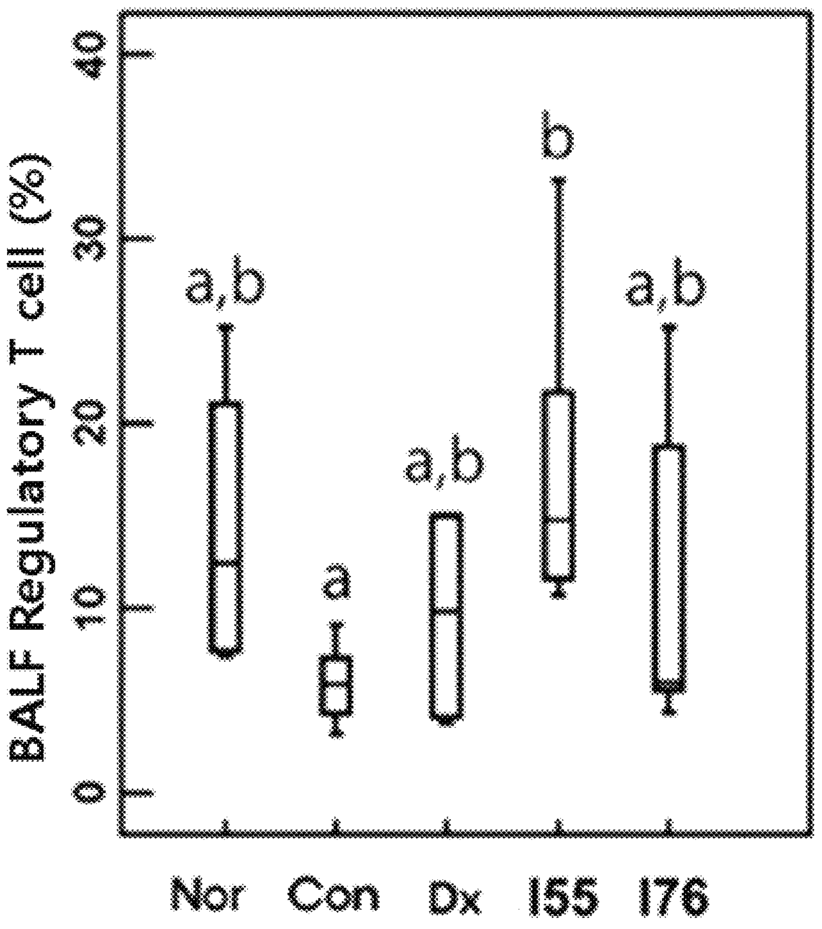

FIG. 17 is a graph of identifying that a distribution rate of Treg cells in the BALF is increased upon administering *Bifidobacterium longum* IM55 or *Lactobacillus plantarum* IM76 into an animal model with induced allergic rhinitis and asthma.

Figure 18:
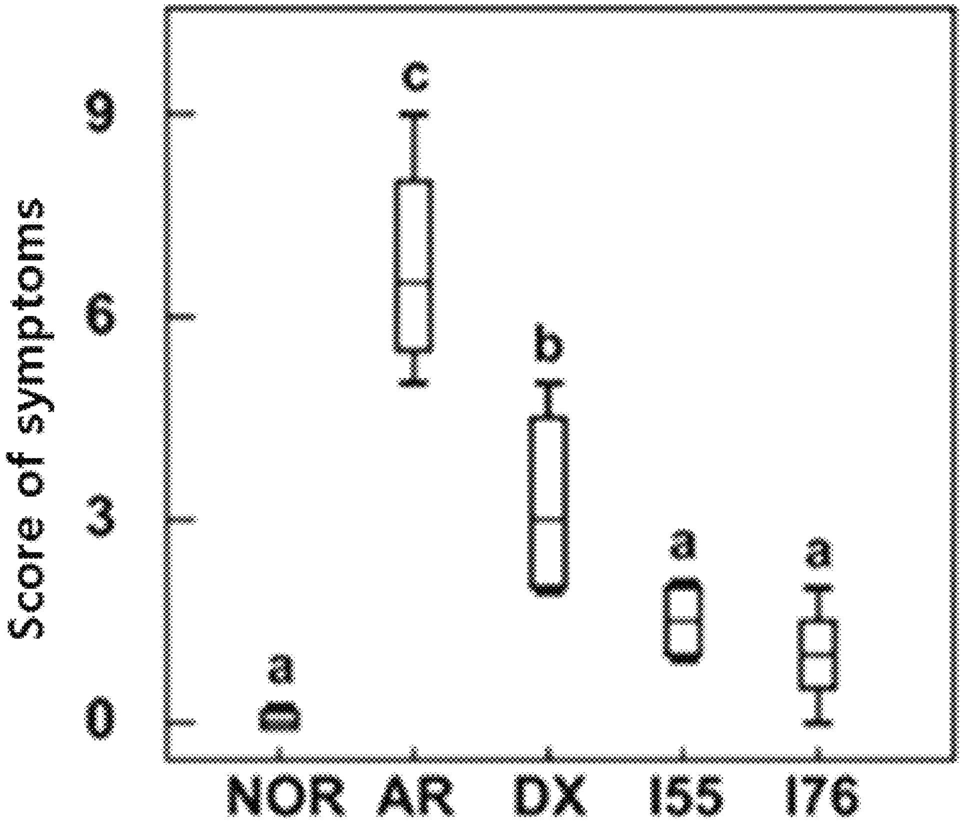

FIG. 18 is a graph of identifying that a score of rhinitis symptoms (sneezing and nasal rubbing) is decreased upon administering *Bifidobacterium longum* IM55 or *Lactobacillus plantarum* IM76 into an animal model with induced allergic rhinitis and asthma (NOR, a normal control group (orally administered with PBS only); AR, a group with an induced disease; DX, a group with an induced disease+intraperitoneally dosed with dexamethasone at 1 mg/kg b.w.; 155, a group with an induced disease+orally dosed with *Bifidobacterium longum* IM55 at $1\times10^9$ CFU/mouse; and 176, a group with an induced disease+orally dosed with *Lactobacillus plantarum* IM76 at $1\times10^9$ CFU/mouse are hereinafter the same as in FIGS. 19 to 26).

Figure 19:
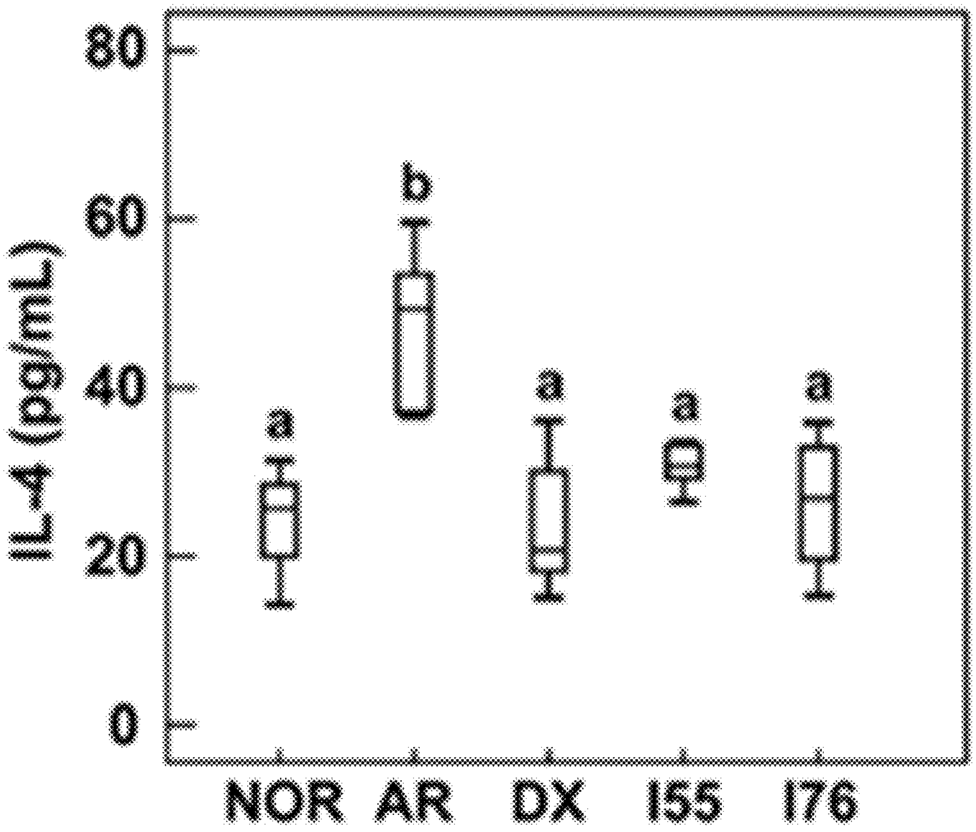

FIG. 19 is a graph of identifying that a concentration of IL-4 in the nasal cavity is decreased upon administering *Bifidobacterium longum* IM55 or *Lactobacillus plantarum* IM76 into an animal model with induced allergic rhinitis and asthma.

Figure 20:
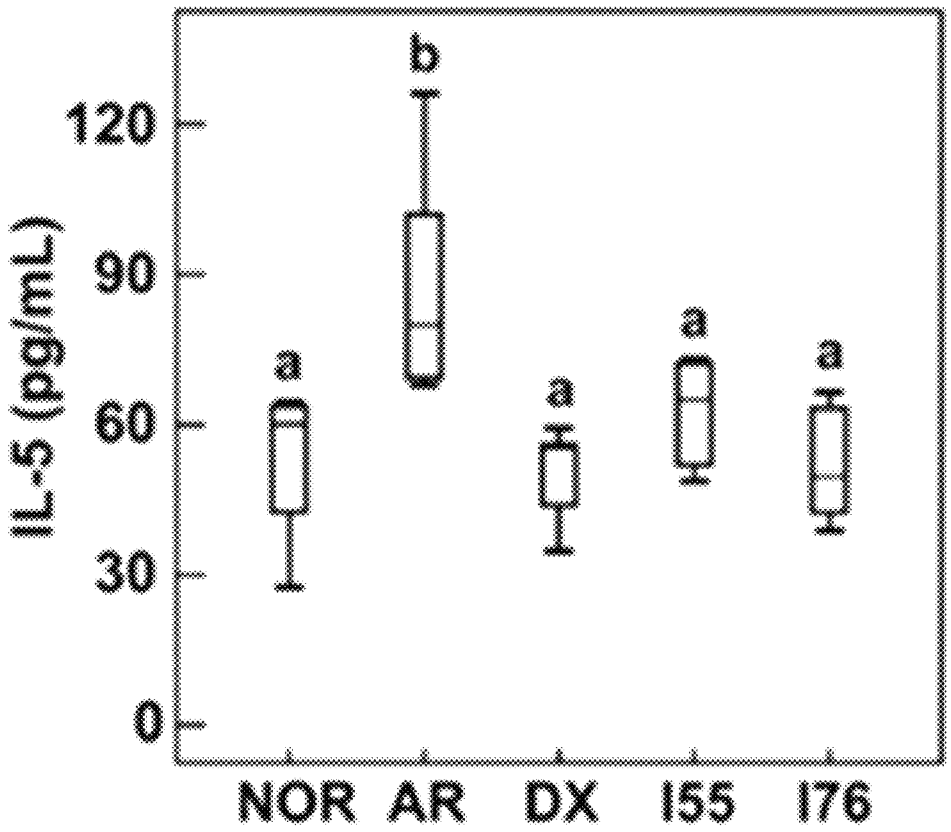

FIG. 20 is a graph of identifying that a concentration of IL-5 in the nasal cavity is decreased upon administering *Bifidobacterium longum* IM55 or *Lactobacillus plantarum* IM76 into an animal model with induced allergic rhinitis and asthma.

Figure 21:
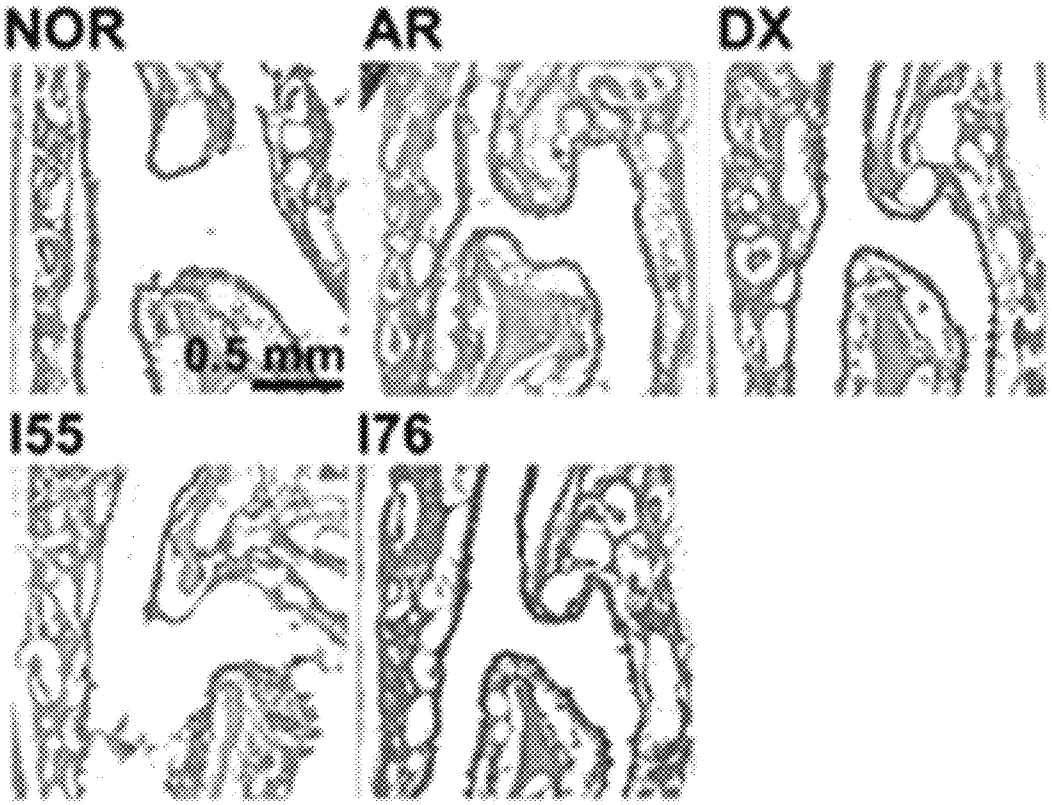

FIG. 21 is a graph of identifying that a disruption of the nasal cavity and an expansion of epithelial cells in the nasal cavity are decreased upon administering *Bifidobacterium longum* IM55 or *Lactobacillus plantarum* IM76 into an animal model with induced allergic rhinitis and asthma.

Figure 22:
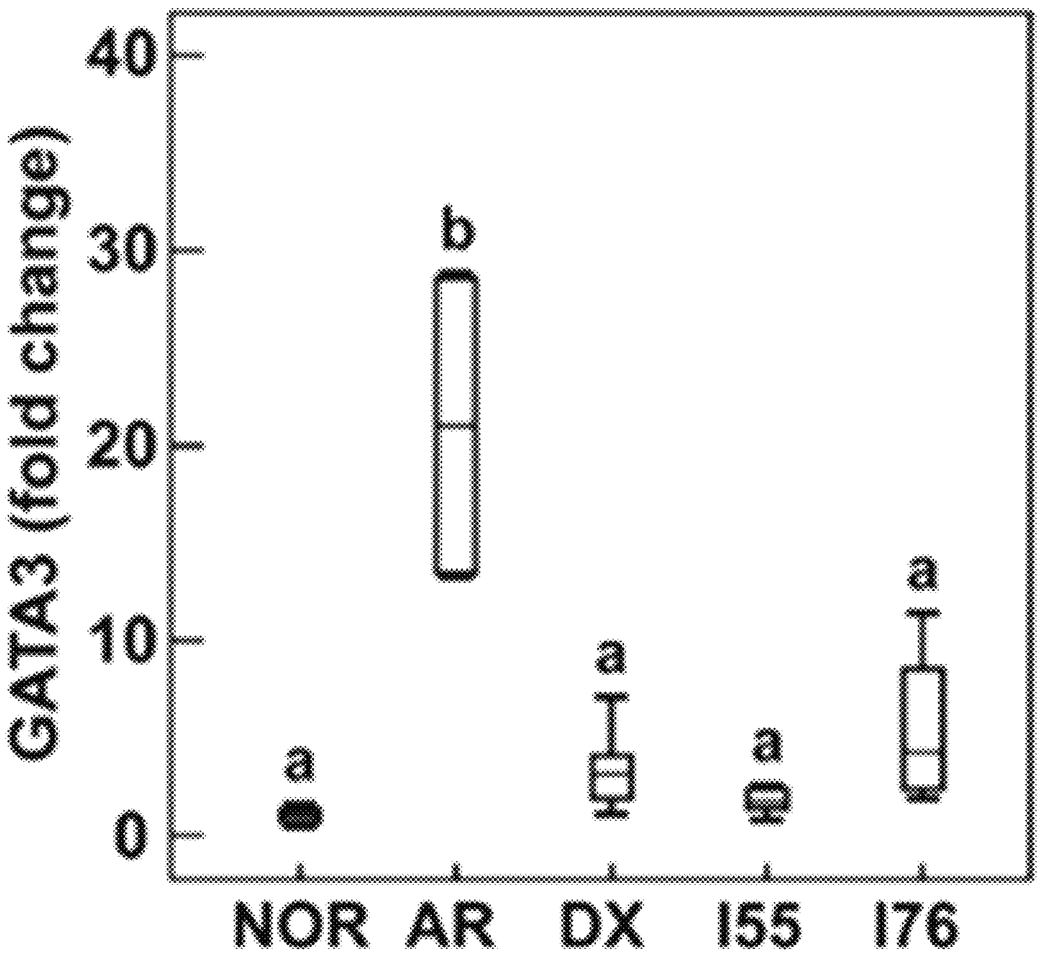

FIG. 22 is a graph of identifying that an expression level of GATA3 in the lung tissues is decreased upon administering *Bifidobacterium longum* IM55 or *Lactobacillus plantarum* IM76 into an animal model with induced allergic rhinitis and asthma.

Figure 23:
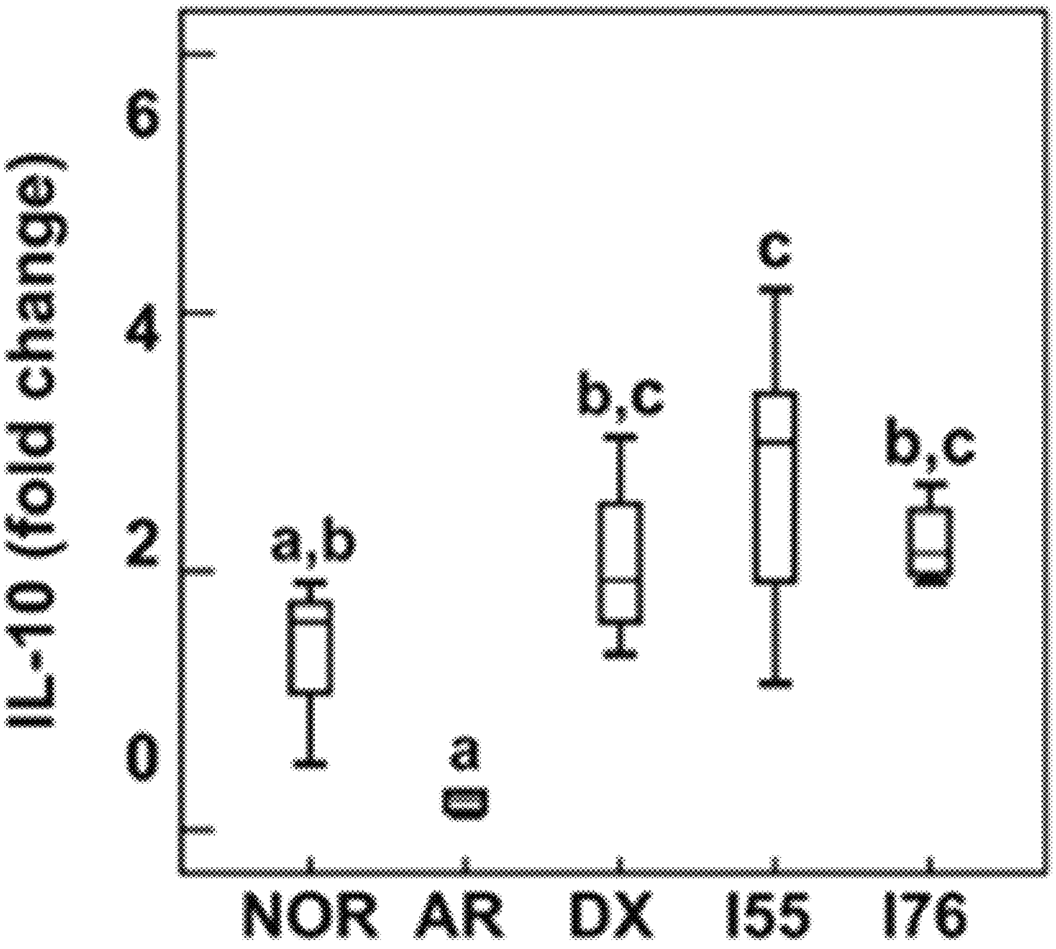

FIG. 23 is a graph of identifying that an expression level of IL-10 in the lung tissues is increased upon administering *Bifidobacterium longum* IM55 or *Lactobacillus plantarum* IM76 into an animal model with induced allergic rhinitis and asthma.

Figure 24:
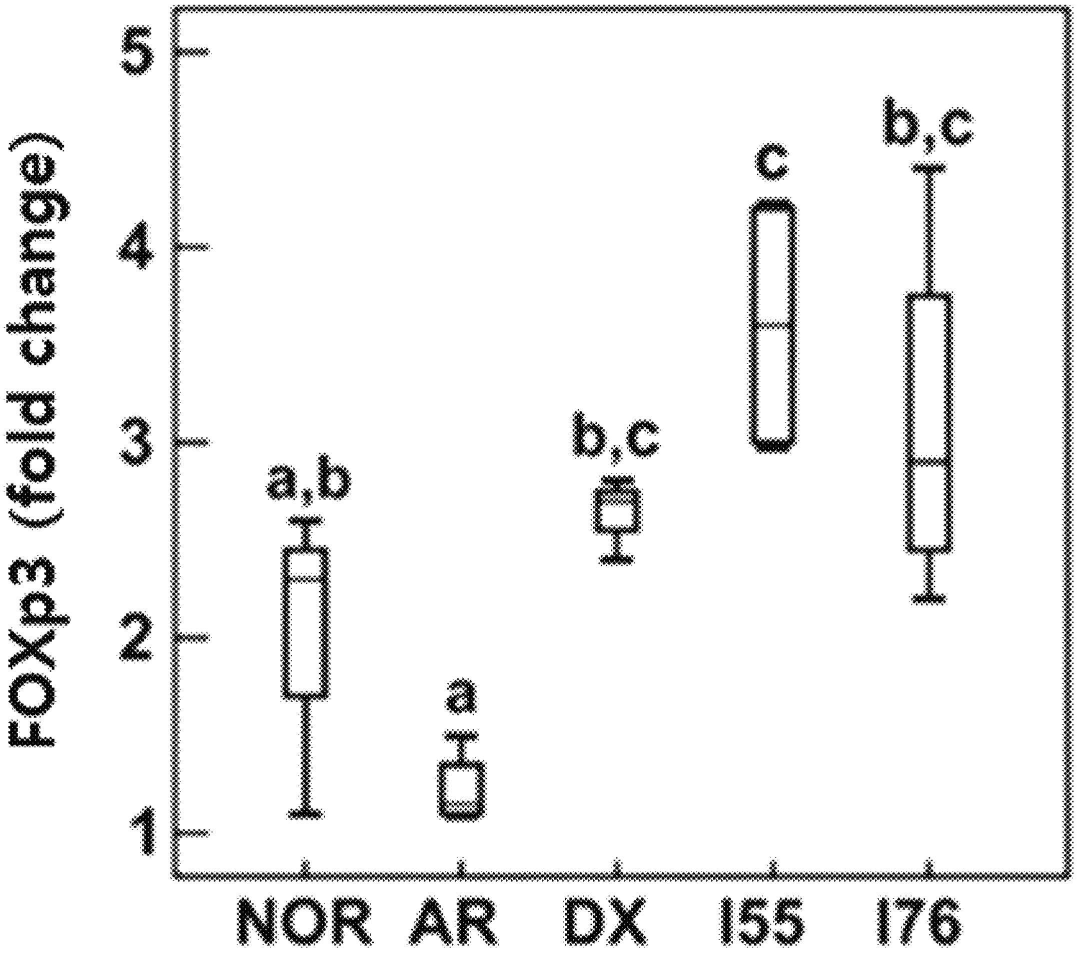

FIG. 24 is a graph of identifying that an expression level of FOXp3 in the lung tissues is increased upon administering *Bifidobacterium longum* IM55 or *Lactobacillus plantarum* IM76 into an animal model with induced allergic rhinitis and asthma.

Figure 25:
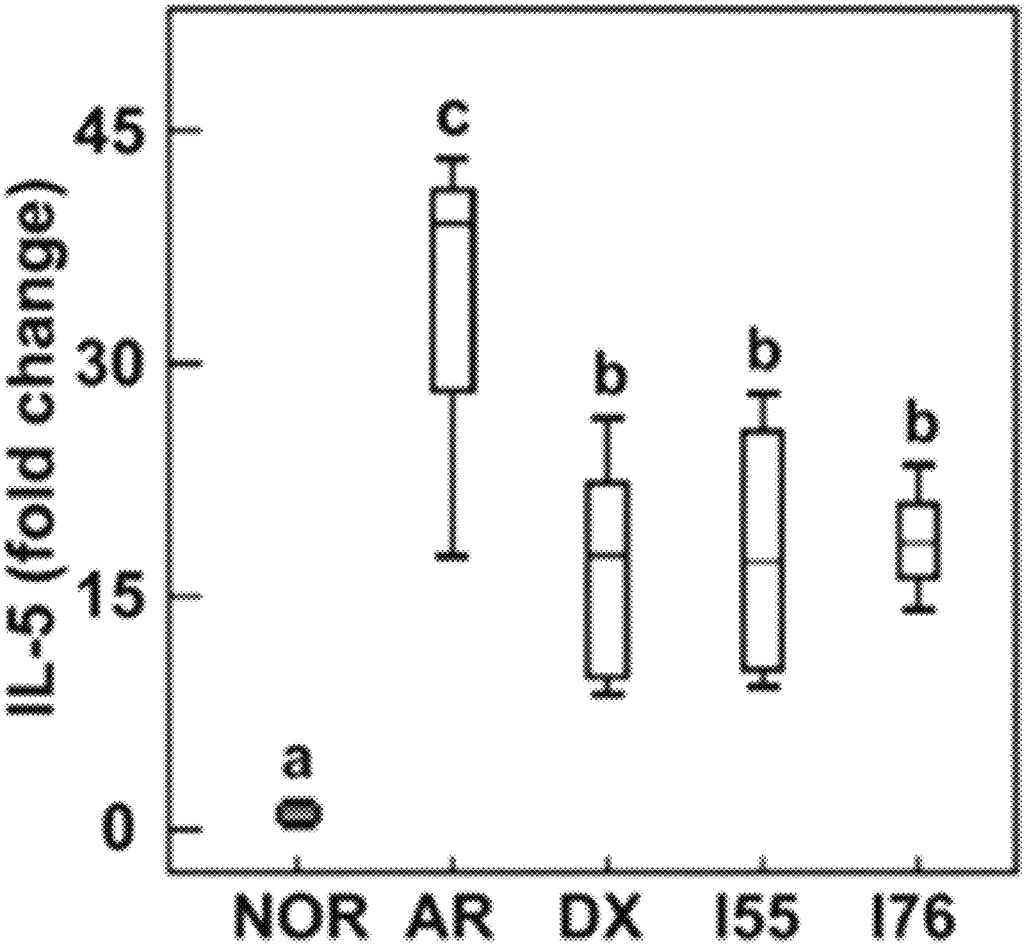

FIG. 25 is a graph of identifying that an expression level of IL-5 in the lung tissues is decreased upon administering *Bifidobacterium longum* IM55 or *Lactobacillus plantarum* IM76 into an animal model with induced allergic rhinitis and asthma.

Figure 26:
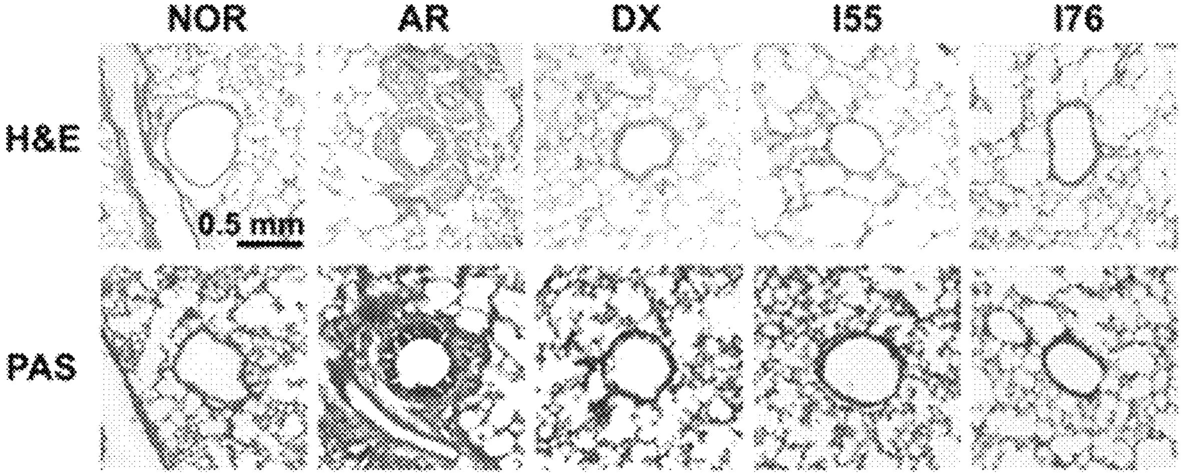

FIG. 26 is a graph of identifying that a degree of inducing inflammations and edema from the lung tissues is decreased upon administering *Bifidobacterium longum* IM55 or *Lactobacillus plantarum* IM76 into an animal model with induced allergic rhinitis and asthma.

Figure 27:
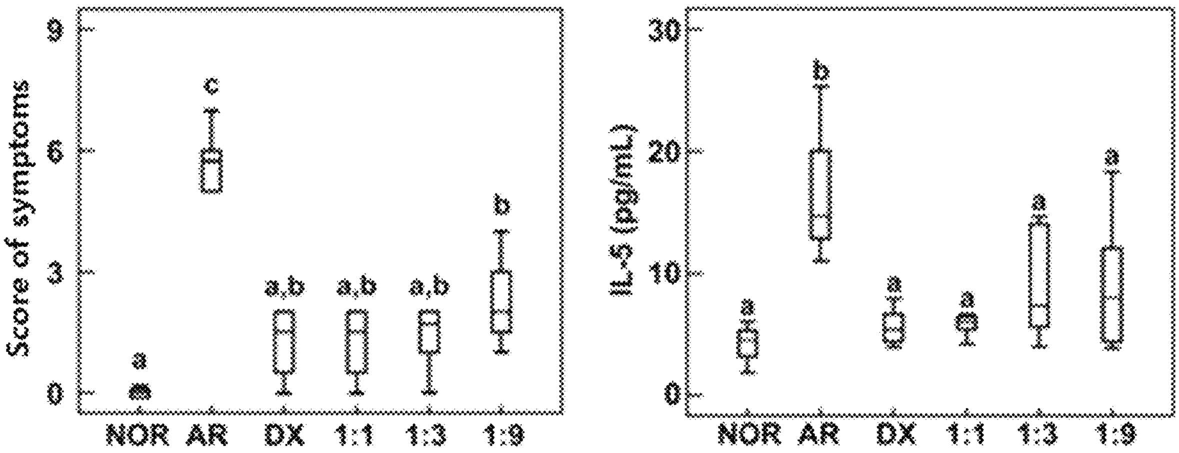

FIG. 27 is a graph of identifying that a score of rhinitis symptoms (sneezing and nasal rubbing) and a concentration of IL-5 in the nasal cavity are decreased upon administering a mixture of *Bifidobacterium longum* IM55 and *Lactobacillus plantarum* IM76 (at a ratio of 1:1, 1:3 and 1:9) into an animal model with induced allergic rhinitis and asthma (NOR, a normal control group (orally administered with PBS only); AR, a group with an induced disease; DX, a group with an induced disease+intraperitoneally dosed with dexamethasone at 1 mg/kg b.w.; 1:1, a group orally dosed with a mixture of *Bifidobacterium longum* IM55 and *Lactobacillus plantarum* IM76 at a ratio of 1:1 (total $1\times10^9$ CFU/mouse); 1:3, a group orally dosed with a mixture of *Bifidobacterium longum* IM55 and *Lactobacillus plantarum* IM76 at a ratio of 1:3 (total $1\times10^9$ CFU/mouse); and 1:9, a group orally dosed with a mixture of *Bifidobacterium longum* IM55 and *Lactobacillus plantarum* IM76 at a ratio of 1:9 (total $1\times10^9$ CFU/mouse) are hereinafter the same as in FIG. 28).

Figure 28:
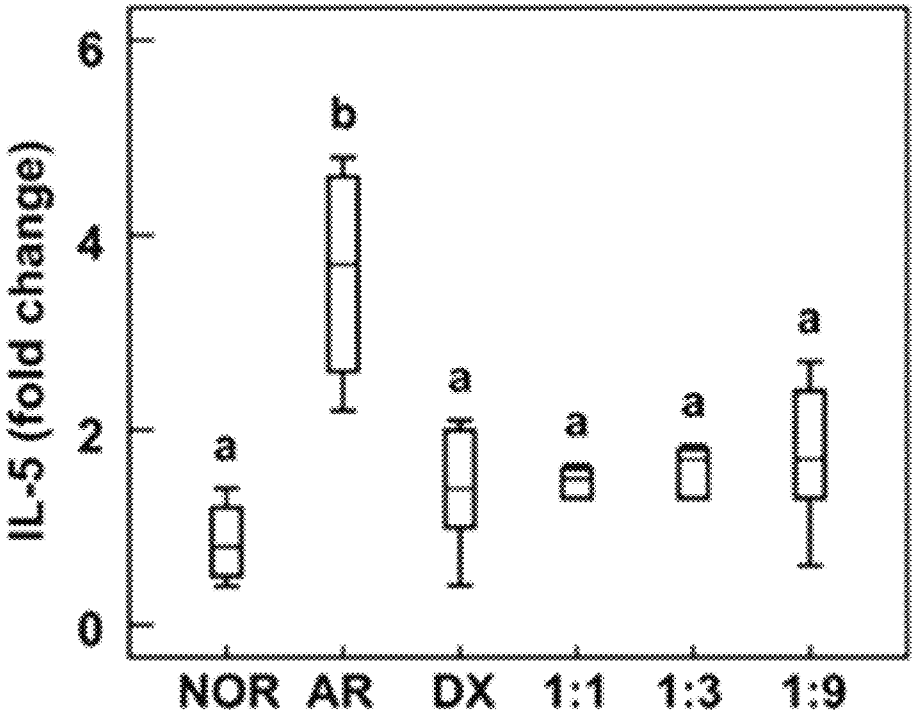

FIG. 28 is a graph of identifying that an expression level of IL-5 in serum is decreased upon administering a mixture of *Bifidobacterium longum* IM55 and *Lactobacillus plantarum* IM76 (at a ratio of 1:1, 1:3 and 1:9) into an animal model with induced allergic rhinitis and asthma.

Figure 29:
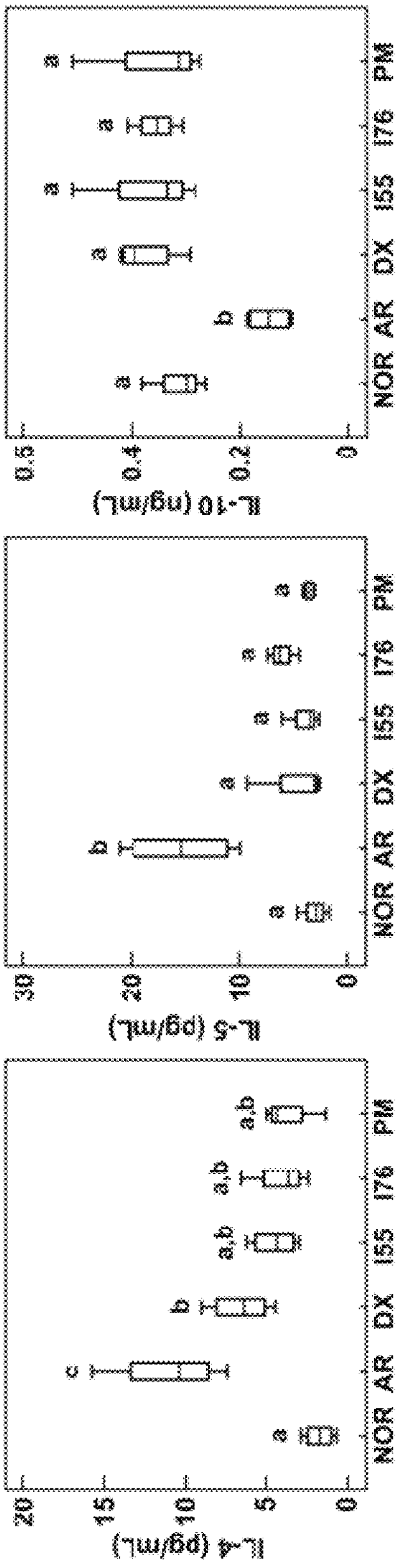

FIG. 29 is a graph of identifying that a concentration of IL-4 and IL-5 in the colon is decreased and a concentration of IL-10 therein is increased upon administering *Bifidobacterium longum* IM55, *Lactobacillus plantarum* IM76 or mixtures thereof into an animal model with induced allergic rhinitis and asthma (NOR, a normal control group (orally administered with PBS only); AR, a group with an induced disease; DX, a group with an induced disease+intraperitoneally dosed with dexamethasone at 1 mg/kg b.w.; 155, a group with an induced disease+orally dosed with *Bifidobacterium longum* IM55 at $1\times10^9$ CFU/mouse; 176, a group with an induced disease+orally dosed with *Lactobacillus plantarum* IM76 at $1\times10^9$ CFU/mouse; and PM, a group with an induced disease+orally dosed with *Bifidobacterium longum* IM55 and *Lactobacillus plantarum* IM76 each at $5\times10^8$ CFU/mouse are hereinafter the same as in FIG. 30).

Figure 30:
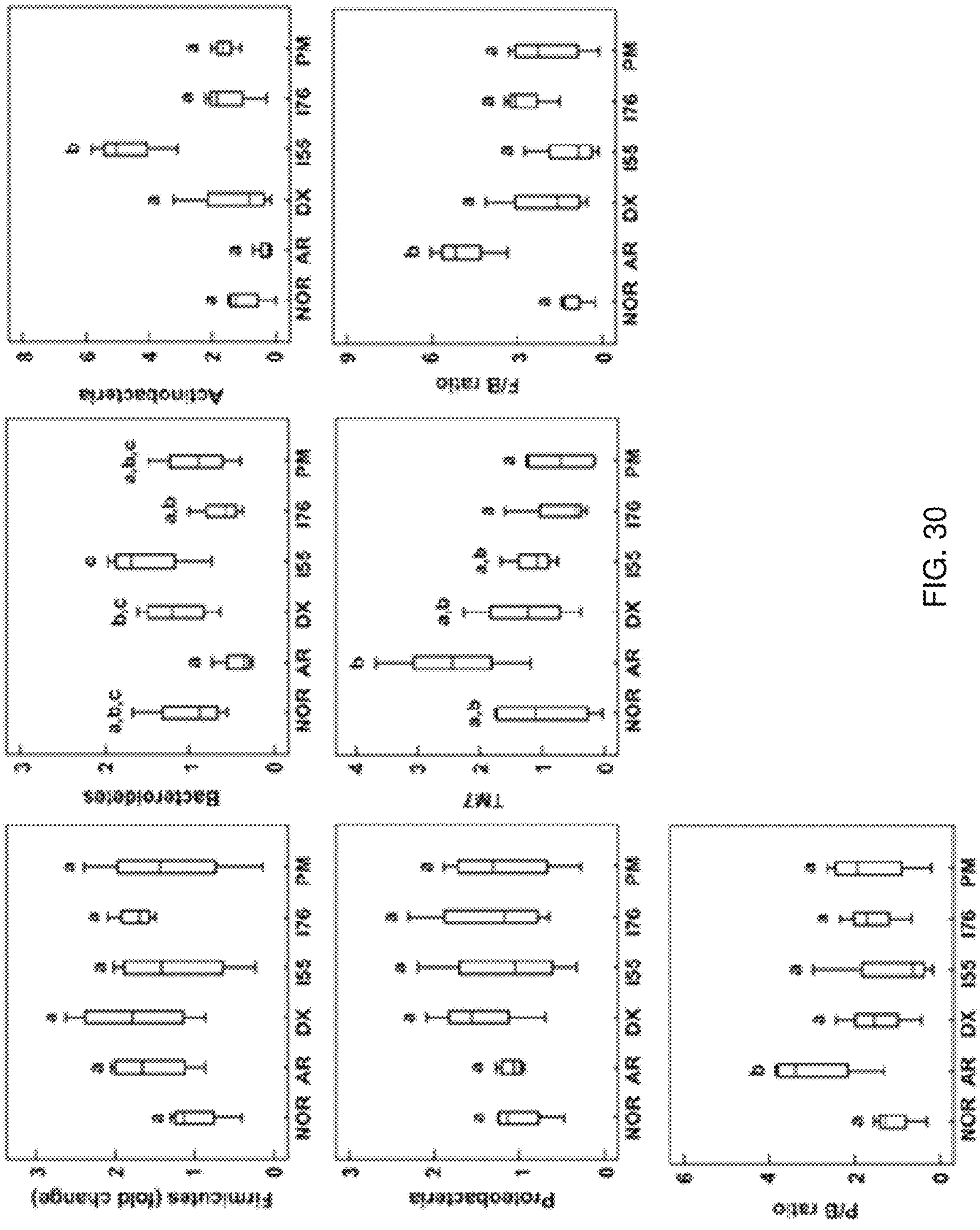

FIG. 30 is a graph of identifying that a constitution of intestinal microorganisms is changed upon administering *Bifidobacterium longum* IM55, *Lactobacillus plantarum* IM76 or mixtures thereof into an animal model with induced allergic rhinitis and asthma.

MODE FOR INVENTION

Hereinafter, the present invention will be described in more detail through exemplary embodiments. However, the following exemplary embodiments are offered only to further clearly illustrate the technical features of the present invention, but are not to be construed to limit the scope of protection of the present invention.

Example 1. Isolation and Identification of Lactic Acid Bacteria (i) Isolation of Lactic Acid Bacteria Excrement of a healthy person in his/her 20's living in Seoul or a healthy person in his/her 60's living in Gurye, Jeollanam-do Province, or cabbage kimchi made at home was inserted and suspended into a GAM broth (Nissui Pharmaceutical, Japan). After that, supernatant thereof was taken and transplanted into an MRS agar medium (Difco, USA) or a GAM agar medium (Nissui Pharmaceutical, Japan). The resulting medium was anaerobically cultured at 37° C. for about 48 hours, after which *Lactobacillus* spp. strains and *Bifidobacterium* spp. strains having formed colonies were isolated therefrom.

(2) Identification of Isolated Lactic Acid Bacteria

With regard to the strains isolated from the human excrement or cabbage kimchi, the species thereof were confirmed and names were given thereto according to gram staining, physiological characteristics, 16S rDNA sequences and the like of those strains. Management nos. and strain names given to the isolated lactic acid bacteria are shown in following tables 1 and 2. The lactic acid bacteria isolated from human excrement were 15 species of *Bifidobacterium longum* (management nos. 51 to 65 of the table 1), 10 species of *Bifidobacterium adolescentis* (management nos. 66 to 75 of the table 1) and 10 species of *Lactobacillus acidophilus* (management nos. 90 to 99 of the table 2), while the lactic acid bacteria isolated from cabbage kimchi were 14 species of *Lactobacillus plantarum* (management nos. 76 to 89 of the table 2).

TABLE 1

| Management no. | Strain name |
|---|---|
| 51 | *Bifidobacterium longum* IM51 |
| 52 | *Bifidobacterium longum* IM52 |
| 53 | *Bifidobacterium longum* IM53 |
| 54 | *Bifidobacterium longum* IM54 |
| 55 | *Bifidobacterium longum* IM55 |
| 56 | *Bifidobacterium longum* IM56 |
| 57 | *Bifidobacterium longum* IM57 |
| 58 | *Bifidobacterium longum* IM58 |
| 59 | *Bifidobacterium longum* IM59 |
| 60 | *Bifidobacterium longum* IM60 |
| 61 | *Bifidobacterium longum* IM61 |
| 62 | *Bifidobacterium longum* IM62 |
| 63 | *Bifidobacterium longum* IM63 |
| 64 | *Bifidobacterium longum* IM64 |
| 65 | *Bifidobacterium longum* IM65 |
| 66 | *Bifidobacterium adolescentis* IM66 |
| 67 | *Bifidobacterium adolescentis* IM67 |
| 68 | *Bifidobacterium adolescentis* IM68 |
| 69 | *Bifidobacterium adolescentis* IM69 |
| 70 | *Bifidobacterium adolescentis* IM70 |
| 71 | *Bifidobacterium adolescentis* IM71 |
| 72 | *Bifidobacterium adolescentis* IM72 |
| 73 | *Bifidobacterium adolescentis* IM73 |
| 74 | *Bifidobacterium adolescentis* IM74 |
| 75 | *Bifidobacterium adolescentis* IM75 |

TABLE 2

| Management no. | Strain name |
|---|---|
| 76 | *Lactobacillus plantarum* IM76 |
| 77 | *Lactobacillus plantarum* IM77 |

TABLE 2-continued

| Management no. | Strain name |
|---|---|
| 78 | *Lactobacillus plantarum* IM78 |
| 79 | *Lactobacillus plantarum* IM79 |
| 80 | *Lactobacillus plantarum* IM80 |
| 81 | *Lactobacillus plantarum* IM81 |
| 82 | *Lactobacillus plantarum* IM82 |
| 83 | *Lactobacillus plantarum* IM83 |
| 84 | *Lactobacillus plantarum* IM84 |
| 85 | *Lactobacillus plantarum* IM85 |
| 86 | *Lactobacillus plantarum* IM86 |
| 87 | *Lactobacillus plantarum* IM87 |
| 88 | *Lactobacillus plantarum* IM88 |
| 89 | *Lactobacillus plantarum* IM89 |
| 90 | *Lactobacillus acidophilus* IM90 |
| 91 | *Lactobacillus acidophilus* IM91 |
| 92 | *Lactobacillus acidophilus* IM92 |
| 93 | *Lactobacillus acidophilus* IM93 |
| 94 | *Lactobacillus acidophilus* IM94 |
| 95 | *Lactobacillus acidophilus* IM95 |
| 96 | *Lactobacillus acidophilus* IM96 |
| 97 | *Lactobacillus acidophilus* IM97 |
| 98 | *Lactobacillus acidophilus* IM98 |
| 99 | *Lactobacillus acidophilus* IM99 |

Out of the strains described in the table 1 above, it was identified that *Bifidobacterium longum* IM55 is a gram-positive *bacillus*, which neither shows a catalase activity nor has a spore. Also, it was shown that 16S rDNA of *Bifidobacterium longum* IM55 has a sequence of SEQ ID NO: 1. As a result of comparing the 16S rDNA sequences of *Bifidobacterium longum* IM55 by means of BLAST search, it was shown that a *Bifidobacterium longum* strain having the same 16S rDNA sequence is not searched at all, and 99% homologous to the 16S rDNA sequence of a known *Bifidobacterium longum* strain. Also, out of the physiological characteristics of *Bifidobacterium longum* IM55, the availability of carbon source was analyzed with a sugar fermentation test using an API kit (model name: API 20 strep; and manufacturer: BioMerieux's, USA), wherein results thereof are shown in a following table 3. In the table 3 below, "+" indicates that the availability of carbon source is positive and "−" indicates that the availability of carbon source is negative.

TABLE 3

| Carbon source | Strain name *Bifidobacterium longum* IM55 | Carbon source | Strain name *Bifidobacterium longum* IM55 |
|---|---|---|---|
| L-tryptophane | − | Gelatin | − |
| Urea | − | Esculin ferric citrate | + |
| D-glucose | + | Glycerol | − |
| D-mannitol | + | D-cellobiose | − |
| D-lactose | + | D-mannose | − |
| D-sucrose | + | D-melezitose | − |
| D-maltose | + | D-raffinose | + |
| Salicin | + | D-sorbitol | + |
| D-xylose | + | D-rhamnose | − |
| L-arabinose | + | D-trehalose | − |

Out of the strains described in the table 2 above, it was identified that *Lactobacillus plantarum* IM76 is a gram-positive *bacillus*. Also, it was shown that 16S rDNA of *Lactobacillus plantarum* IM76 has a sequence of SEQ ID NO: 2. As a result of comparing the 16S rDNA sequences of *Lactobacillus plantarum* IM76 by means of BLAST search, it was shown that a *Lactobacillus plantarum* strain having the same 16S rDNA sequence is not searched at all, and such sequence was 99% homologous to the 16S rDNA sequence of a known *Lactobacillus plantarum* strain. Also, out of the physiological characteristics of *Lactobacillus plantarum* IM76, the availability of carbon source was analyzed with a sugar fermentation test using an API kit (model name: API 50 CHL; and manufacturer: BioMerieux's, USA), wherein results thereof are shown in a following table 4. In the table 4 below, "+" indicates that the availability of carbon source is positive and "−" indicates that the availability of carbon source is negative.

TABLE 4

| Carbon source | Strain name *Lactobacillus plantarum* IM76 | Carbon source | Strain name *Lactobacillus plantarum* IM76 |
|---|---|---|---|
| Glycerol | − | Salicin | + |
| Erythritol | − | Cellobiose | + |
| D-arabinose | − | Maltose | + |
| L-arabinose | + | Lactose | + |
| D-ribose | + | Melibiose | + |
| D-xylose | − | Sucrose | + |
| L-xylose | − | Trehalose | + |
| D-adonitol | − | Inulin | − |
| Methyl-β-D-xylopyranoside | − | Melezitose | − |
| D-galactose | + | Raffinose | + |
| D-glucose | + | Starch | − |
| D-fructose | + | Glycogen | − |
| D-mannose | + | Xylitol | − |
| L-sorbose | − | Gentiobiose | + |
| L-rhamnose | − | D-turanose | + |
| Dulcitol | − | D-lyxose | − |
| Inositol | − | D-tagatose | − |
| Mannitol | + | D-fucose | − |
| Sorbitol | + | L-fucose | − |
| α-methyl-D-mannoside | − | D-arabitol | − |
| α-methly-D-glucoside | − | L-arabitol | − |
| N-acetyl-glucosamine | + | Gluconate | + |
| Amygdalin | + | 2-keto-gluconate | − |
| Arbutin | + | 5-keto-gluconate | − |
| Esculin | + | | |

Example 2. Test on the Inflammation Reaction Inhibiting Effect of Lactic Acid Bacteria (1) Test on the Inflammation Reaction Inhibiting Effect of Lactic Acid Bacteria on Macrophage A six-week old C57BL/6J male mouse (20-23 g) was purchased from Raonbio Co., Ltd. 2 ml of sterilized 4% thioglycolate was intraperitoneally administered into the mouse, which was then anesthetized in 96 hours later. After that, 8 ml of RPMI 1640 medium was intraperitoneally administered to the mouse. In 5 to 10 minutes later, the RPMI medium (including macrophage) was intraperitoneally extracted again from the mouse, then centrifuged on condition of 1000 rpm for 10 minutes, and then washed twice again with the RPMI 1640 medium. The macrophage was plated into a 24-well plate at $0.5\times10^6$ cells per well, then cultured for 24 hours, and then unattached cells were removed therefrom. The macrophage culture fluid was treated with a test material, i.e., lactic acid bacteria as well as an inflammation reaction inducer, i.e., lipopolysaccharide (LPS) for 90 minutes or 24 hours, and then supernatant and cells were obtained therefrom. At that time, a treatment concentration of lactic acid bacteria was $1\times10^4$ CFU/ml. Also, in order to compare the effects of lactic acid bacteria, various prebiotics were used as the test material.

An expression level of TNF-α from said obtained supernatant was measured by means of an ELISA kit. Also, the expression level of p65 (NF-κB), p-p65 (phosphor-NF-κB) and β-actin was measured from said obtained cells by means of an immunoblotting method. Particularly, 50 μg of the supernatant was taken and subjected to electrophoresis in SDS 10% (w/v) polyacrylamide gel for one and half an hour. The electrophoresed sample was transferred onto a nitrocellulose paper on condition of 100 V and 400 mA for one hour and 10 minutes. The nitrocellulose paper, onto which the sample was transferred, was subjected to blocking by means of 5% skim milk for 30 minutes, then washed with PBS-Tween three times for five minutes each, and then subjected to reaction overnight with an addition of primary antibodies (Santa Cruz Biotechnology, the U.S.) at a ratio of 1:100. After that, such paper was washed three times for ten minutes each, and subjected to reaction with the addition of secondary antibodies (Santa Cruz Biotechnology, the U.S.) at a ratio of 1:1000 for one hour and 20 minutes. Then, such paper was washed three times for 15 minutes each, then subjected to fluorescent color formation, then developed, and then the intensity of chromophore band was measured. The results of testing the inflammation reaction inhibiting effect of lactic acid bacteria on macrophage are shown in following tables 5 to 7.

TABLE 5

| Test material for treating macrophage | NF-κB activation inhibition rate (p-p65/p65) | TNF-α expression inhibition rate |
|---|---|---|
| Untreated | − | − |
| *Bifidobacterium longum* IM51 | + | + |
| *Bifidobacterium longum* IM52 | ++ | ++ |
| *Bifidobacterium longum* IM53 | ++ | ++ |
| *Bifidobacterium longum* IM54 | ++ | + |
| *Bifidobacterium longum* IM55 | +++ | +++ |
| *Bifidobacterium longum* IM56 | ++ | ++ |
| *Bifidobacterium longum* IM57 | + | + |
| *Bifidobacterium longum* IM58 | + | + |
| *Bifidobacterium longum* IM59 | + | + |
| *Bifidobacterium longum* IM60 | + | + |
| *Bifidobacterium longum* IM61 | + | + |
| *Bifidobacterium longum* IM62 | + | + |
| *Bifidobacterium longum* IM53 | + | + |
| *Bifidobacterium longum* IM64 | + | + |
| *Bifidobacterium longum* IM65 | + | + |
| *Bifidobacterium adolescentis* IM66 | +++ | + |
| *Bifidobacterium adolescentis* IM67 | + | + |
| *Bifidobacterium adolescentis* IM68 | + | + |
| *Bifidobacterium adolescentis* IM69 | + | + |
| *Bifidobacterium adolescentis* IM70 | + | + |
| *Bifidobacterium adolescentis* IM71 | + | + |

TABLE 6

| Test material for treating macrophage | NF-κB activation inhibition rate (p-p65/p65) | TNF-α expression inhibition rate |
|---|---|---|
| *Bifidobacterium adolescentis* IM72 | + | + |
| *Bifidobacterium adolescentis* IM73 | + | + |
| *Bifidobacterium adolescentis* IM74 | + | + |
| *Bifidobacterium adolescentis* IM75 | + | + |
| *Lactobacillus plantarum* IM76 | +++ | +++ |
| *Lactobacillus plantarum* IM77 | + | ++ |
| *Lactobacillus plantarum* IM78 | + | + |
| *Lactobacillus plantarum* IM79 | + | ++ |
| *Lactobacillus plantarum* IM80 | + | + |
| *Lactobacillus plantarum* IM81 | +++ | +++ |

TABLE 6-continued

| Test material for treating macrophage | NF-κB activation inhibition rate (p-p65/p65) | TNF-α expression inhibition rate |
|---|---|---|
| *Lactobacillus plantarum* IM82 | + | + |
| *Lactobacillus plantarum* IM83 | + | + |
| *Lactobacillus plantarum* IM84 | + | + |
| *Lactobacillus plantarum* IM85 | + | + |
| *Lactobacillus plantarum* IM86 | + | + |
| *Lactobacillus plantarum* IM87 | ++ | ++ |
| *Lactobacillus plantarum* IM88 | + | + |
| *Lactobacillus plantarum* IM89 | + | + |
| *Lactobacillus acidophilus* IM90 | + | + |
| *Lactobacillus acidophilus* IM91 | +++ | +++ |
| *Lactobacillus acidophilus* IM92 | + | + |
| *Lactobacillus acidophilus* IM93 | + | + |

TABLE 7

| Test material for treating macrophage | NF-κB activation inhibition rate (p-p65/p65) | TNF-α expression inhibition rate |
|---|---|---|
| *Lactobacillus acidophilus* IM94 | + | + |
| *Lactobacillus acidophilus* IM95 | + | + |
| *Lactobacillus acidophilus* IM96 | + | + |
| *Lactobacillus acidophilus* IM97 | + | + |
| *Lactobacillus acidophilus* IM98 | + | + |
| *Lactobacillus acidophilus* IM99 | + | + |
| Inulin | ++ | ++ |
| Citrus pectin | ++ | + |
| Carrageenan | + | − |
| Trehalose | + | − |
| Lactulose | + | − |
| Cyclodextrin | + | − |
| Carboxymethyl cellulose | + | + |
| Gelatin | + | + |
| Chitosan | ++ | ++ |
| Alginic acid | + | + |
| Fructo-oligosaccharide | + | + |
| Defatted soybean protein | + | + |
| Apple pectin | + | ++ |
| Arabino-galactan | + | ++ |
| Xylan | + | − |

Inhibition rate: —, <10%; +, 10-30%; ++, 30-60%; +++, >60%

As a result of tests in the tables 5 to 7, it was identified that the inflammation reaction inhibiting effect on macrophage differs depending on types of lactic acid bacteria. Particularly, in case of *Bifidobacterium* spp. lactic acid bacteria and *Lactobacillus* spp. lactic acid bacteria, it was identified that an inflammation reaction inhibiting effect differs not only depending on species but also depending on strains, even if those strains are the same species. Out of those strains, in case of *Bifidobacterium longum* IM55 and *Lactobacillus plantarum* IM76, it was identified that an NF-kB activation inhibition rate and a TNF-α expression inhibition rate are all high at the same time.

Also, in case of chitosan, inulin and citrus pectin as prebiotics, it was identified that an NF-kB activation inhibition rate and a TNF-α expression inhibition rate are excellent compared to other prebiotics.

(2) Test on the Inflammation Reaction Inhibiting Effect of Lactic Acid Bacteria on Dendritic Cells Immune cells were isolated from the bone marrow of a C57BL/6 mouse (male, 20-23 g) by using RPMI 1640 containing 10% FBS, 1% antibiotics, 1% glutamax and 0.1% mercaptoethanol, then treated with RBC lysis buffer, and then washed. Said cells were divided into each well of a 24-well plate, then treated with GM-CSF and IL-4 at a ratio of 1:1000, and then cultured. On a 5th day of culture, the cells were replaced with a new medium, then collected on an 8th day thereof, and then used as dendritic cells. After that, the dendritic cells were plated into a 24-well plate at $0.5\times10^6$ cells per well, then treated with a test material, i.e., lactic acid bacteria, as well as an inflammation reaction inducer, i.e., lipopolysaccharide (LPS) for 90 minutes or 24 hours, and then supernatant and cells were obtained therefrom. At that time, a treatment concentration of lactic acid bacteria was $1\times10^4$ CFU/ml. Also, in order to compare the effects of lactic acid bacteria, various prebiotics were used as the test material.

An expression level of IL-10 and IL-12 was measured from said obtained supernatant by means of an ELISA kit. Also, the expression level of p65 (NF-κB), p-p65 (phosphor-NF-κB) and β-actin was measured from the cells, which have been obtained after being treated with the test material for 90 minutes, by means of the same immunoblotting method as in Example 2.(1) above. The results of testing the inflammation reaction inhibiting effect of lactic acid bacteria on dendritic cells are shown in following tables 8 to 10.

TABLE 8

| Test material for treating dendritic cells | NF-κB activation inhibition rate (p-p65/p65) | IL-12 expression inhibition rate | IL-10 expression increasing rate |
|---|---|---|---|
| Untreated | − | − | − |
| *Bifidobacterium longum* IM51 | + | + | + |
| *Bifidobacterium longum* IM52 | ++ | − | − |
| *Bifidobacterium longum* IM53 | + | − | − |
| *Bifidobacterium longum* IM54 | + | + | + |
| *Bifidobacterium longum* IM55 | +++ | ++ | +++ |
| *Bifidobacterium longum* IM56 | ++ | ++ | ++ |
| *Bifidobacterium longum* IM57 | + | + | + |
| *Bifidobacterium longum* IM58 | + | + | − |
| *Bifidobacterium longum* IM59 | + | + | − |
| *Bifidobacterium longum* IM60 | + | + | − |
| *Bifidobacterium longum* IM61 | + | + | − |
| *Bifidobacterium longum* IM62 | + | + | − |
| *Bifidobacterium longum* IM53 | + | + | − |
| *Bifidobacterium longum* IM64 | + | + | + |
| *Bifidobacterium longum* IM65 | + | + | − |
| *Bifidobacterium adolescentis* IM66 | +++ | ++ | − |
| *Bifidobacterium adolescentis* IM67 | + | + | + |
| *Bifidobacterium adolescentis* IM68 | + | + | + |
| *Bifidobacterium adolescentis* IM69 | + | + | − |
| *Bifidobacterium adolescentis* IM70 | + | + | − |
| *Bifidobacterium adolescentis* IM71 | + | + | − |

TABLE 9

| Test material for treating dendritic cells | NF-κB activation inhibition rate (p-p65/p65) | IL-12 expression inhibition rate | IL-10 expression increasing rate |
|---|---|---|---|
| *Bifidobacterium adolescentis* IM72 | + | + | − |
| *Bifidobacterium adolescentis* IM73 | + | + | + |
| *Bifidobacterium adolescentis* IM74 | + | + | + |
| *Bifidobacterium adolescentis* IM75 | + | + | + |
| *Lactobacillus plantarum* IM76 | ++ | ++ | ++ |
| *Lactobacillus plantarum* IM77 | + | + | + |
| *Lactobacillus plantarum* IM78 | + | + | + |
| *Lactobacillus plantarum* IM79 | + | + | − |
| *Lactobacillus plantarum* IM80 | + | + | + |
| *Lactobacillus plantarum* IM81 | + | + | + |
| *Lactobacillus plantarum* IM82 | + | + | − |
| *Lactobacillus plantarum* IM83 | + | + | + |

TABLE 9-continued

| Test material for treating dendritic cells | NF-κB activation inhibition rate (p-p65/p65) | IL-12 expression inhibition rate | IL-10 expression increasing rate |
|---|---|---|---|
| *Lactobacillus plantarum* IM84 | + | + | + |
| *Lactobacillus plantarum* IM85 | + | + | + |
| *Lactobacillus plantarum* IM86 | ++ | + | − |
| *Lactobacillus plantarum* IM87 | + | ++ | + |
| *Lactobacillus plantarum* IM88 | + | + | − |
| *Lactobacillus plantarum* IM89 | + | + | − |
| *Lactobacillus acidophilus* IM90 | + | + | + |
| *Lactobacillus acidophilus* IM91 | + | + | − |
| *Lactobacillus acidophilus* IM92 | + | + | − |
| *Lactobacillus acidophilus* IM93 | + | + | + |

TABLE 10

| Test material for treating dendritic cells | NF-κB activation inhibition rate (p-p65/p65) | IL-12 expression inhibition rate | IL-10 expression increasing rate |
|---|---|---|---|
| *Lactobacillus acidophilus* IM94 | + | + | − |
| *Lactobacillus acidophilus* IM95 | + | + | − |
| *Lactobacillus acidophilus* IM96 | + | + | − |
| *Lactobacillus acidophilus* IM97 | + | + | − |
| *Lactobacillus acidophilus* IM98 | + | + | − |
| *Lactobacillus acidophilus* IM99 | + | + | + |
| Inulin | ++ | + | + |
| Citrus pectin | ++ | ++ | ++ |
| Carrageenan | + | + | − |
| Trehalose | + | + | + |
| Lactulose | + | + | − |
| Cyclodextrin | + | + | − |
| Carboxymethyl cellulose | + | + | − |
| Gelatin | + | + | + |
| Chitosan | ++ | + | ++ |
| Alginic acid | + | + | + |
| Fructo-oligosaccharide | + | + | − |
| Defatted soybean protein | + | + | + |
| Apple pectin | + | + | − |
| Arabino-galactan | + | + | + |
| Xylan | + | + | ++ |

Inhibition rate: −, <10%; +, 10-30%; ++, 30-60%; +++, >60%

Increasing rate: −, <10%; +, 10-50%; ++, 50-100%; +++, >100%

As a result of tests in the tables 8 to 10, it was identified that the inflammation reaction inhibiting effect on dendritic cells differs depending on types of lactic acid bacteria. Particularly, in case of *Bifidobacterium* spp. lactic acid bacteria and *Lactobacillus* spp. lactic acid bacteria, it was identified that an inflammation reaction inhibiting effect differs not only depending on species, but also depending on strains, even if those strains are the same species. In particular, a part of the strains showed results, in which IL-12 expression is increased. On the other hand, most of the strains showed results, in which IL-10 expression is decreased. Out of those strains, in case of *Bifidobacterium longum* IM55 and *Lactobacillus plantarum* IM76, it was identified that an NF-kB activation inhibition rate and an IL-12 expression inhibition rate are highest, and an IL-10 expression increasing rate is highest at the same time.

Also, in case of chitosan, inulin and citrus pectin as prebiotics, it was identified that the NF-kB activation inhibition rate, the IL-12 expression inhibition rate and the IL-10 expression increasing rate are excellent compared to other prebiotics.

From Example 2 above, out of various lactic acid bacteria, *Bifidobacterium longum* IM55 and *Lactobacillus plantarum* IM76 showed the most excellent inflammation reaction inhibiting effect. Also, out of various prebiotics, it was identified that chitosan, inulin and citrus pectin show an excellent inflammation reaction inhibiting effect.

Example 3. Evaluation of the Immunity Regulatory Effect of Lactic Acid Bacteria (1) Cell Differentiation Rate To control, prevent, alleviate or treat allergic diseases, particularly the diseases caused by a type 1 hypersensitivity reaction, it is important to decrease a production of IgE antibodies and increase a production of regulatory T cells (Treg cells) of releasing IL-10 upon an immune reaction to an allergen. It is known that an allergic reaction becomes more complicated not only by means of mediators made by mast cells, basophils or the like, but also by means of an action of cytokines secreted from those cells, and a part of symptoms shown as the allergic reaction result from an action of those cytokines. Cytokines such as TNF-α, IL-4, IL-5, IL-6, IL-13, etc., are made in the mast cells, and those cytokines play a role in gathering neutrophils and eosinophils. Also, IL-4 and IL-13 secreted from the mast cells activate B cells to make IgE antibodies, and IL-5 plays a role in gathering and activating eosinophils. Cytokines such as IL-4 and IL-5 are generally classified into Th2 cytokines because many of those cytokines are secreted from Th2 cells, and the cytokines secreted from mast cells and Th2 cells bind to respective receptors, and thus act to induce an interaction between cells and amplify an allergic reaction. Also, an allergic shock symptom may occur when TNF-α, a representative proinflammatory cytokine, is systemically produced in quantity in an allergy state.

Thus, in order to evaluate an immunity regulatory effect of the lactic acid bacteria isolated from excrement or cabbage kimchi, an influence of the lactic acid bacteria on the immune reactions of spleen cells was measured by measuring an inhibition rate of differentiation into cells of secreting said cytokines and an increasing rate of differentiation into Treg cells.

Particularly, a spleen was isolated from a C56BL/6J mouse, then crushed, then suspended in an RPMI 1640 medium containing 10% FCS, and then CD4 T cells were isolated by using a CD4 T cell isolation kit (MiltenyiBiotec, Bergisch Gladbach, Germany). The isolated CD4 T cells were divided into a 12-well plate at $5\times10^5$ cells per well. After that, the cells were cultured in each well with an addition of anti-CD3, anti-CD28, IL-2 and IL-12 to induce a differentiation of T cells into Th1 cells; with the addition of anti-CD3, anti-CD28, IL-2 and IL-4 to induce the differentiation of T cells into Th2 cells; with the addition of anti-CD3, anti-CD28, IL-6 and TGF-β to induce the differentiation of T cells into Th17 cells; and with the addition of anti-CD3 and anti-CD28 to induce the differentiation of T cells into Treg cells, and a test material, i.e., lactic acid bacteria were inserted thereinto at $1\times10^5$ CFU per well, and then cultured for four days. Also, in order to compare the effects of lactic acid bacteria, various prebiotics were used as the test material.

After that, a differentiation potency of the T cells isolated from the spleen into Th1, Th2, Th17 and Treg cells was measured. Particularly, the cells of culture fluid were stained with anti-FOXp3 or anti-IL-17A antibodies, after which a distribution of Th1, Th2, Th17 and Treg cells was analyzed by means of a FACS (fluorescence-activated cell sorting) device (C6 Flow Cytometer® System, San Jose, CA, USA), wherein results thereof are shown in following tables 11 to 13. In the tables 11 to 13 below, the lactic acid bacteria are shown without species names thereof, and are given strain names assigned by the present inventors.

TABLE 11

| Test material for treating spleen | Differentiation inhibition rate | | | Differentiation increasing rate |
|---|---|---|---|---|
| T cells | Th1 cell | Th2 cell | Th17 cell | Treg cell |
| Untreated | − | − | − | − |
| IM51 | + | + | + | + |
| IM52 | ++ | − | − | − |
| IM53 | + | − | + | + |
| IM54 | + | + | + | + |
| IM55 | +++ | +++ | +++ | +++ |
| IM56 | ++ | + | + | + |
| IM57 | ++ | − | + | + |
| IM58 | ++ | − | + | − |
| IM59 | + | + | + | − |
| IM60 | + | + | + | − |
| IM61 | ++ | + | ++ | + |
| IM62 | ++ | + | ++ | + |
| IM63 | + | + | + | + |
| IM64 | ++ | ++ | + | + |
| IM65 | + | + | + | + |
| IM66 | +++ | + | ++ | + |
| IM67 | ++ | + | ++ | + |
| IM68 | ++ | + | ++ | + |
| IM69 | + | + | + | + |
| IM70 | ++ | + | ++ | + |
| IM71 | ++ | + | ++ | + |

TABLE 12

| Test material for treating spleen | Differentiation inhibition rate | | | Differentiation increasing rate |
|---|---|---|---|---|
| T cells | Th1 cell | Th2 cell | Th17 cell | Treg cell |
| IM72 | + | + | + | + |
| IM73 | ++ | + | + | + |
| IM74 | + | + | + | + |
| IM75 | +++ | + | + | ++ |
| IM76 | ++ | +++ | +++ | +++ |
| IM77 | + | + | + | + |
| IM78 | + | + | ++ | ++ |
| IM79 | + | + | ++ | + |
| IM80 | + | ++ | + | + |
| IM81 | + | + | ++ | + |
| IM82 | + | + | + | + |
| IM83 | + | ++ | ++ | + |
| IM84 | + | + | ++ | + |
| IM85 | + | + | + | + |
| IM86 | + | + | + | + |
| IM87 | + | + | ++ | + |
| IM88 | + | + | + | + |
| IM89 | ++ | + | ++ | + |
| IM90 | + | + | + | + |
| IM91 | + | + | + | + |
| IM92 | + | + | + | + |
| IM93 | ++ | + | ++ | + |

TABLE 13

| Test material for treating spleen | Differentiation inhibition rate | | | Differentiation increasing rate |
|---|---|---|---|---|
| T cells | Th1 cell | Th2 cell | Th17 cell | Treg cell |
| IM94 | + | + | + | + |
| IM95 | + | + | + | + |
| IM96 | ++ | ++ | ++ | + |

TABLE 13-continued

| Test material for treating spleen | Differentiation inhibition rate | | | Differentiation increasing rate |
|---|---|---|---|---|
| T cells | Th1 cell | Th2 cell | Th17 cell | Treg cell |
| IM97 | + | + | + | + |
| IM98 | + | + | + | − |
| IM99 | + | + | + | + |
| P1 | + | + | + | + |
| P2 | + | +++ | ++ | ++ |
| P3 | +++ | ++ | + | + |
| P4 | + | + | + | + |
| P5 | + | ++ | − | ++ |
| P6 | ++ | + | ++ | + |
| P7 | ++ | ++ | ++ | − |
| P8 | + | ++ | + | + |
| P9 | + | ++ | + | + |
| P10 | + | + | ++ | + |
| P11 | + | + | + | ++ |
| P12 | + | + | + | + |
| P13 | + | + | + | − |
| P14 | + | + | + | − |
| P15 | ++ | + | ++ | − |

Inhibition rate: −, <10%; +, 10-30%; ++, 30-60%; +++, >60%

Increasing rate: −, <10%; +, 10-50%; ++, 50-100%; +++, >100%

P1: inulin; P2: citrus pectin; P3: carrageenan; P4: trehalose; P5: lactulose; P6: cyclodextrin; P7: carboxymethyl cellulose; P8: gelatin; P9: chitosan; P10: alginic acid; P11: fructooligosaccharide; P12: defatted soybean protein; P13: apple pectin; P14: arabino-galactan; and P15: xylan As a result of experiments in the tables 11 to 13, it was identified that a differentiation rate of T cells differs depending on types of lactic acid bacteria. Particularly, in case of *Bifidobacterium* spp. lactic acid bacteria, an inhibition rate of differentiation into Th1, Th2 and Th17 cells and an increasing rate of differentiation into Treg cells differ depending on types of lactic acid bacteria, and a part of the lactic acid bacteria showed results, in which a Th2 cell inhibition rate and a Treg cell increasing rate are opposite to those of other lactic acid bacteria. Out of those lactic acid bacteria, it was identified for *Bifidobacterium longum* IM55 that the inhibition rate of differentiation into Th1, Th2 and Th17 cells is highest, and an increasing rate of differentiation into Treg cells is highest at the same time. Also, *Lactobacillus* spp. lactic acid bacteria showed results, similar to *Bifidobacterium* spp. lactic acid bacteria, in which the inhibition and increasing rates of cell differentiation differ depending on types of lactic acid bacteria. Out of those lactic acid bacteria, it was identified for *Lactobacillus plantarum* IM76 that the inhibition rate of differentiation into Th1, Th2 and Th17 cells and the increasing rate of differentiation into Treg cells are highest.

(2) Cytokine Expression Rate

Also, an expression rate of transcription factors and cytokines of Th1, Th2, Th17 and Treg cells differentiated from the spleen T cells was measured. Particularly, expression levels were respectively analyzed by means of qRT-PCR with regard to T-bet, IFN-γ and IL-12 from culture fluid for inducing a Th1 cell differentiation; GATA3 and IL-5 from culture fluid for inducing a Th2 cell differentiation; RORγt and IL-17 from culture fluid for inducing a Th17 cell differentiation; and Foxp3 and IL-10 from culture fluid for inducing a Treg cell differentiation. A following table 14 shows results in such a way that a sequence of a primer used for qRT-PCR corresponds to that of an amplification target. Also, the results of measuring the expression rates of transcription factors and cytokines of Th1, Th2, Th17 and Treg cells differentiated from the spleen T cells are shown in following tables 15 and 16. In the tables 15 and 16 below, the lactic acid bacteria are shown without species names thereof, and are given strain names assigned by the present inventors.

TABLE 14

| Amplification target | Primer type | Primer sequence |
|---|---|---|
| T-bet | Forward (SEQ ID NO: 3) | 5'-CCTCTTCTATCCAACCAGTATC-3' |
| | Reverse (SEQ ID NO: 4) | 5'-CTCCGCTTCATAACTGTGT-3' |
| IFN-γ | Forward (SEQ ID NO: 5) | 5'-TCAAGTGGCATAGATGTGGAAGAA-3' |
| | Reverse (SEQ ID NO: 6) | 5'-TGGCTCTGCAGGATTTTCATG-3' |
| GATA3 | Forward (SEQ ID NO: 7) | 5'-GAAGGCATCCAGACCCGAAAC-3' |
| | Reverse (SEQ ID NO: 8) | 5'-ACCCATGGCGGTGACCATGC-3' |
| IL-5 | Forward (SEQ ID NO: 9) | 5'-AAAGAGAAGTGTGGCGAGGAGAGAC-3' |
| | Reverse (SEQ ID NO: 10) | 5'-CCTTCCATTGCCCACTCTGTACTCATC-3' |
| RORγt | Forward (SEQ ID NO: 11) | 5'-ACAGCCACTGCATTCCCAGTTT-3' |
| | Reverse (SEQ ID NO: 12) | 5'-TCTCGGAAGGACTTGCAGACAT-3' |
| IL-17 | Forward (SEQ ID NO: 13) | 5'-TTTAACTCCCTTGGCGCAAAA-3' |
| | Reverse (SEQ ID NO: 14) | 5'-CTTTCCCTCCGCATTGACAC-3' |
| FOXp3 | Forward (SEQ ID NO: 15) | 5'-CCCATCCCCAGGAGTCTT-3' |
| | Reverse (SEQ ID NO: 16) | 5'-ACCATGACTAGGGGCACTGTA-3' |
| IL-10 | Forward (SEQ ID NO: 17) | 5'-ATGCTGCCTGCTCTTACTGACTG-3' |
| | Reverse (SEQ ID NO: 18) | 5'-CCCAAGTAACCCTTAAAGTCCTGC-3' |
| GAPDH | Forward (SEQ ID NO: 19) | 5'-TGCAGTGGCAAAGTGGAGAT-3' |
| | Reverse (SEQ ID NO: 20) | 5'-TTTGCCGTGAGTGGAGTCAT-3' |

TABLE 15

| Test material for treating spleen | Expression inhibition rate | | | | | | Expression increasing rate | |
|---|---|---|---|---|---|---|---|---|
| T cells | T-bet | IFN-γ | GATA3 | IL-5 | RORγt | IL-17 | FOXp3 | IL-10 |
| Untreated | − | − | − | − | − | − | − | − |
| IM51 | + | ++ | + | + | + | + | + | + |
| IM52 | ++ | + | − | + | − | + | − | − |
| IM53 | + | + | − | + | + | ++ | + | − |
| IM54 | + | + | + | ++ | + | + | ++ | + |
| IM55 | +++ | + | +++ | +++ | +++ | +++ | +++ | +++ |
| IM56 | ++ | + | + | ++ | + | ++ | + | ++ |
| IM57 | ++ | ++ | − | + | + | + | + | + |
| IM58 | ++ | ++ | − | ++ | + | + | − | − |
| IM59 | + | + | + | + | + | + | − | + |
| IM60 | + | ++ | + | ++ | + | + | − | − |
| IM61 | ++ | + | + | ++ | ++ | ++ | + | − |
| IM62 | ++ | + | + | ++ | ++ | ++ | + | + |
| IM63 | + | ++ | + | + | + | + | + | − |
| IM64 | ++ | + | ++ | ++ | + | + | + | + |
| IM65 | + | + | + | + | + | + | + | − |
| IM66 | ++ | + | + | + | ++ | ++ | + | + |
| IM67 | + | + | + | + | ++ | + | + | + |
| IM68 | ++ | ++ | + | + | ++ | ++ | + | + |
| IM69 | + | + | + | + | + | + | + | − |
| IM70 | ++ | + | + | + | ++ | ++ | + | + |
| IM71 | ++ | + | + | + | ++ | ++ | + | + |
| IM72 | + | ++ | + | + | + | + | + | + |
| IM73 | ++ | + | + | + | + | + | + | + |
| IM74 | + | + | + | + | + | + | + | + |

TABLE 16

| Test material for treating spleen | Expression inhibition rate | | | | | | Expression increasing rate | |
|---|---|---|---|---|---|---|---|---|
| T cells | T-bet | IFN-γ | GATA3 | IL-5 | RORγt | IL-17 | FOXp3 | IL-10 |
| IM75 | ++ | + | + | + | + | + | ++ | + |
| IM76 | ++ | ++ | +++ | +++ | +++ | +++ | +++ | +++ |
| IM77 | + | + | + | ++ | + | + | + | + |
| IM78 | + | + | + | + | ++ | ++ | ++ | + |
| IM79 | + | + | + | ++ | ++ | ++ | + | − |
| IM80 | + | + | ++ | + | + | + | + | + |
| IM81 | + | + | + | + | ++ | ++ | + | + |
| IM82 | + | + | + | + | + | + | + | + |
| IM83 | + | ++ | ++ | ++ | ++ | ++ | + | + |
| IM84 | + | + | + | + | ++ | ++ | + | + |
| IM85 | + | ++ | + | ++ | + | + | + | + |
| IM86 | + | + | + | + | + | + | + | − |
| IM87 | + | + | + | + | ++ | ++ | + | + |
| IM88 | + | ++ | + | + | + | ++ | + | − |
| IM89 | ++ | + | + | + | ++ | + | + | − |
| IM90 | + | + | + | ++ | + | + | + | + |
| IM91 | + | + | + | ++ | + | + | + | − |
| IM92 | + | + | + | + | + | + | + | − |
| IM93 | ++ | + | + | ++ | ++ | + | + | + |
| IM94 | + | + | + | + | + | + | + | + |
| IM95 | + | + | + | + | + | + | + | − |
| IM96 | ++ | + | ++ | ++ | ++ | ++ | + | − |
| IM97 | + | + | + | + | + | + | + | + |
| IM98 | + | + | + | + | + | + | − | − |
| IM99 | + | + | + | + | + | + | + | + |

Inhibition rate: −, <10%; +, 10-30%; ++, 30-60%; +++, >60%

Increasing rate: −, <10%; +, 10-50%; ++, 50-100%; +++, >100%

As a result of measurements in the tables 15 and 16, it was identified that a rate of change in cytokine expression differs depending on types of lactic acid bacteria. Particularly, in case of *Bifidobacterium* spp. lactic acid bacteria, a part of the lactic acid bacteria showed results, in which an inhibition rate of GATA3 and IL-5 expressions is opposite to that of other lactic acid bacteria. Out of those lactic acid bacteria, it was identified for *Bifidobacterium longum* IM55 that an inhibition rate of T-bet, IFN-γ, GATA3, IL-5, RORγt and IL-17 expressions is highest, and an increasing rate of FOXp3 and IL-10 expressions is highest at the same time. Also, in case of *Lactobacillus* spp. lactic acid bacteria, a part of the lactic acid bacteria show results, similar to *Bifidobacterium* spp. lactic acid bacteria, in which a rate of change in cytokine expression differs, too. Out of those lactic acid bacteria, it was identified for *Lactobacillus plantarum* IM76 that an inhibition rate of T-bet, IFN-γ, GATA3, IL-5, RORγt and IL-17 expressions is highest, and an increasing rate of FOXp3 and IL-10 expressions is highest at the same time.

Example 4. Test on the Inflammation Reaction Inhibiting Effect of IM55 or IM76

Out of the lactic acid bacteria isolated in Example 1 above, a test was performed on the inflammation reaction inhibiting effect of *Bifidobacterium longum* IM55 and *Lactobacillus plantarum* IM76.

Figure 1:
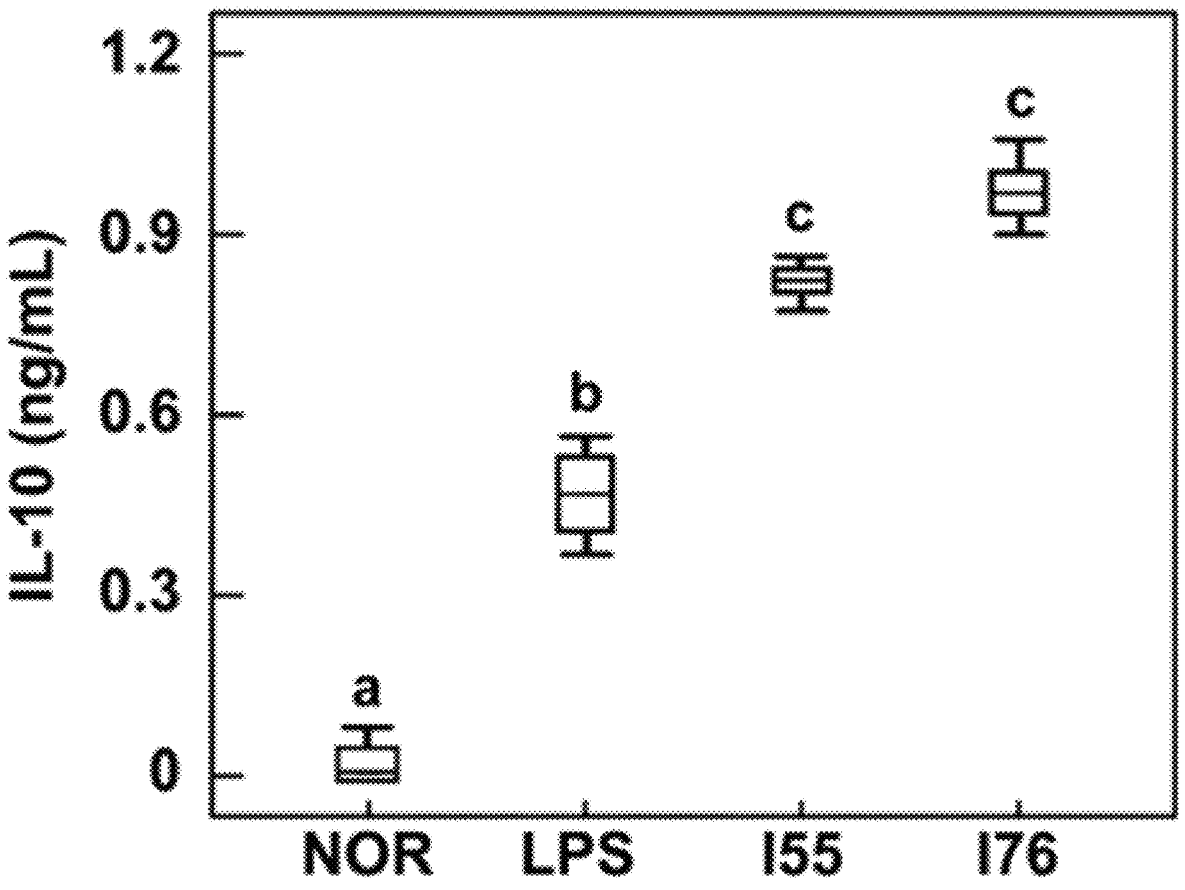
FIG. 1 is a graph of identifying that a concentration of IL-10 is increased upon treating macrophage with *Bifidobacterium longum* IM55 or *Lactobacillus plantarum* IM76 (NOR, a normal control group; LPS, a group with induced inflammation reactions; I55, a group with induced inflammation reactions+dosed with *Bifidobacterium longum* IM55 at $1\times10^5$ CFU/ml; and 176, a group with induced inflammation reactions+dosed with *Lactobacillus plantarum* IM76 at $1\times10^5$ CFU/ml are hereinafter the same as in FIGS. 2 to 4).

(1) Test on the Inflammation Reaction Inhibiting Effect of IM55 or IM76 on Macrophage A seven week-old BALB/c female mouse (20-22 g) was purchased from Raonbio Co., Ltd., and acclimated for seven days before an experiment. 2 ml of 4% thioglycolate was intraperitoneally administered into the mouse, which was then sacrificed in 96 hours later. Peritoneal cavity fluids were collected with 10 ml of RPMI 1640, then centrifuged on condition of 300×g for 10 minutes, and then washed with RPMI 1640. Cells were plated into a 12-well microplate at $0.5\times10^6$ cells per well, then cultured in an RPMI 1640 medium containing 1% antibiotic-antimycotic and 10% FBS at 37° C. for 20 hours, and then washed three times. Attached cells were used as macrophage. To measure an effect of IM55 or IM76 on cytokine expressions, macrophage at $1\times10^6$ cells/well was treated with lactic acid bacteria at $1\times10^5$ CFU/ml as well as an inflammation reaction inducer, i.e., the LPS for 20 hours. An expression level of each cytokine was measured by means of the same ELISA kit as in Example 2.(1) above. As a result of the measurement, it was identified that an expression of IL-10 is increased and an expression of IL-12 is inhibited upon administration of IM55 or IM76 (FIGS. 1 and 2).

(2) Test on the Inflammation Reaction Inhibiting Effect of IM55 or IM76 on Dendritic Cells Mouse marrow cells were collected from a seven week-old BALB/c female mouse (20-22 g) with RPMI 1640 according to a known method (Immunopharmacol. Immunotoxicol., 2016, 38, 447-454). $2\times10^6$ collected cells were seeded into a 12-well plate and cultured in an RPMI 1640 medium containing rGM-CSF at 20 ng/ml, 10% FBS, 1% antibiotic-antimycotic and gentamycin at 15 μg/ml.

To measure an effect of IM55 or IM76 on cytokine expressions, said cells were replaced with a conditioned medium on 3rd and 6th days of culture to remove granulocytes therefrom, and then treated with lactic acid bacteria at $1\times10^5$ CFU/ml and the LPS at 100 ng/ml on an 8th day of culture. An expression level of each cytokine was measured by means of the same ELISA kit as in Example 2.(2) above. As a result of the measurement, it was identified that an expression of IL-10 is increased and an expression of TNF-α is inhibited upon administration of IM55 or IM76 (FIGS. 3 and 4).

From the results of Example 4 above, it might be seen that novel lactic acid bacteria, i.e., *Bifidobacterium longum* IM55 and *Lactobacillus plantarum* IM76 show an excellent inflammation reaction inhibiting effect, and thus show an excellent effect on preventing, alleviating and treating inflammatory diseases.

Example 5. Evaluation of the Immunity Regulatory Effect of IM55 or IM76

A rate of T cell differentiation was analyzed by means of a method similar to Example 3 above, in order to evaluate the immunity regulatory effect of *Bifidobacterium longum* IM55 and *Lactobacillus plantarum* IM76 out of the lactic acid bacteria isolated from Example 1 above.

Particularly, a spleen was sterilely isolated from a seven week-old BALB/c female mouse (20-22 g), then appropriately crushed, and then treated with tris-buffered ammonium chloride. The resulting cells were suspended in an RPMI 1640 medium containing 10% FCS, after which T cells were isolated from a cell suspension by using Pan T Cell Isolation Kit II. The cells were respectively cultured with an addition of anti-CD28 (1 μg/ml), anti-CD3 (1 μg/ml), rIL-4 (10 μg/ml) and rIL-2 (10 μg/ml) to induce a differentiation of the isolated T cells ($1\times10^5$ cells/well) into Th2 cells; and with the addition of anti-CD28 (1 μg/ml) and anti-CD3 (1 μg/ml) to induce the differentiation of T cells ($1\times10^5$ cells/well) into Treg cells, and the cells were also respectively cultured for four days with the addition of IM55 or IM76 at $1\times10^5$ CFU/ml per well. RNA was isolated from those cells, after which an expression level of IL-10, GATA3, FOXp3 and IL-5 was analyzed by carrying out qRT-PCR. The same qRT-PCR was performed as in Example 3 above, and by using the same primer as in the table 14 above.

As a result of the analysis, it was identified for treatment with IM55 or IM 76 that an expression level of GATA3 and IL-5 is decreased to inhibit a differentiation into Th2 cells (FIGS. 5 and 6), while an expression level of FOXp3 and IL-10 is increased to promote a differentiation into Treg cells (FIGS. 7 and 8).

From the results of Example 5 above, it might be seen that novel lactic acid bacteria, i.e., *Bifidobacterium longum* IM55 and *Lactobacillus plantarum* IM76 show an excellent immunity regulatory effect, and thus show an excellent effect on preventing, alleviating and treating immune diseases.

Example 6. Evaluation of the Alleviation Effect of Lactic Acid Bacteria on Rhinitis and Asthma (1)

Bronchoalveolar lavage (BAL), which is performed together with bronchial endoscopy, has been widely used to collect cells and other soluble components from an epithelial mucous layer, which covers respiratory tracts and pulmonary alveoli. Bronchoalveolar lavage fluid (BALF) includes not only various proteins in a blood flow, but also proteins secreted from various cell types including epithelial cells and inflammatory cells. The BALF is generally used to diagnose bronchial asthma, bronchitis or lung disease, or analyze pathological conditions thereof. Thus, in order to identify an effect of alleviating rhinitis and asthma, indicators related to anti-rhinitis and anti-asthma effects were analyzed from serum and lung tissues as well as the BALF.

(1) Experimental Method

Seven week-old BALB/C female mice (21-23 g) were acclimated for one week on condition of a controlled environment with humidity of 50%, temperature of 25° C., and light/dark cycle of 12:12 hours. After that, 20 μg of allergy-inducing ovalbumin (OVA) and 2 mg of aluminum hydroxide (Alum) were suspended into 0.2 ml of phosphate buffered saline (PBS: pH 7.4) and intraperitoneally injected into each of the mice on initial and 14th days of an experiment. Then, 100 μg of the OVA was dissolved in 10 μl of distilled water, and intranasally smeared onto each of the mice to induce allergic rhinitis and asthma therefrom on 26th, 27th and 28th days of the experiment. Meanwhile, a test drug, i.e., lactic acid bacteria were orally administered into each of the mice once daily for a total of five days from 26th to 30th days of the experiment. Also, dexamethasone, which was used as a positive control drug instead of lactic acid bacteria, was intraperitoneally administered at a dose of 1 mg/kg b.w. Further, in case of the mice of a normal group, allergic rhinitis and asthma were not induced therefrom, but only the phosphate buffered saline (PBS: pH 7.4) was orally administered thereinto instead of the OVA and the test drug. Furthermore, in case of the mice of a control group, allergic rhinitis and asthma were induced therefrom, and only the phosphate buffered saline (PBS: pH 7.4) was orally administered thereinto as the test drug. After an end of the experiment, the mice were anesthetized, after which blood, lung tissues and the BALF were collected therefrom. Serum was isolated from the blood collected by means of centrifugation, and used as an assay sample.

Indicators related to anti-rhinitis and anti-asthma effects were analyzed from serum, the BALF and lung tissues by using various analysis methods. Each analysis method and indicators analyzed thereby are as follows.

Enzyme-linked immunosorbent assay (ELISA): IL-10, IL-5, IL-6, IL-4, IgE, etc.

FACS (fluorescence-activated cell sorting): Distribution of T cells (Th1: $CD4^+$/IFN-$\gamma^+$; Th2: $CD4^+$/IL-$4^+$; Treg: $CD4^+$/FOXp$3^+$; Th17: $CD4^+$/IL-$17^+$), Distribution of eosinophils ($CD11b^+$, Siglec-$F^+$)

(2) Experimental Results

As a result of the experiment, it was identified that an expression of IL-5, IgE and IL-4, i.e., the indicators related to rhinitis and asthma, is remarkably inhibited in serum of a group dosed with IM55 or IM76 (table 17 and FIGS. 9 to 11). Also, it was identified that an amount of IL-5 and IL-4, i.e., the indicators related to rhinitis and asthma, is remarkably decreased and a ratio of Th2 cells and eosinophils is remarkably decreased in the BALF, too (table 18 and FIGS. 12 to 15). Furthermore, it was identified that an expression of IL-10, related to an effect of preventing and treating rhinitis and asthma, is increased and a ratio of Treg cells is increased in the BALF (table 18 and FIGS. 16 and 17).

TABLE 17

| Classification of experimental groups | Inhibition rate | | |
|---|---|---|---|
| | IL-5 | IgE | IL-4 |
| Con | – | – | – |
| IM55 | +++ | ++ | +++ |
| IM76 | ++ | + | ++ |
| Dx | ++ | +++ | +++ |

TABLE 18

| Classification of experimental | Inhibition rate | | | | Increasing rate | |
|---|---|---|---|---|---|---|
| groups | IL-5 | IL-4 | Th2 cell | Eosinophils | IL-10 | Treg cell |
| Con | – | – | – | – | – | – |
| IM55 | +++ | +++ | ++ | +++ | +++ | +++ |
| IM76 | ++ | +++ | +++ | +++ | +++ | + |
| Dx | +++ | +++ | +++ | +++ | ++ | – |

Inhibition rate: –, <10%; +, 10-30%; ++, 30-60%; +++, >60%

Increasing rate: –, <10%; +, 10-50%; ++, 50-100%; +++, >100%

Example 7. Evaluation of the Alleviation Effect of Lactic Acid Bacteria on Rhinitis and Asthma (2)

(1) Experimental Method

The OVA-induced allergic rhinitis models were prepared with reference to a known method (Oh et al., Immunopharmacol. Immunotoxicol., 2013, 35, 678-686). Particularly, the mice were randomly divided into six groups (n=8 per group). For five groups, the OVA (20 μg) diluted in aluminum potassium sulfate solution was intraperitoneally injected into the mice thereof on 1st and 14th days of an experiment. 100 μg of the OVA was dissolved in 10 μl of distilled water and intranasally smeared onto each of said mice to induce allergic rhinitis and asthma therefrom on 26th, 27th and 28th days of the experiment. Meanwhile, a test material (IM55 ($1\times10^9$ CFU/mouse), IM76 ($1\times10^9$ CFU/mouse), dexamethasone (1 mg/kg) or saline solution) was administered into the mice once daily for a total of five days from 26th to 30th days of the experiment. In case of the mice of a normal group, allergic rhinitis and asthma were not induced therefrom, but only the saline solution was administered thereinto. The mice were subjected to irritation by intranasally administering the OVA (10 μl/nostril, dissolved in 10 mg/ml of saline solution) into both nasal cavities thereof, after which the number of sneezing and nasal rubbing behaviors (score of rhinitis symptoms) was counted for 10 minutes on a 31st day of the experiment.

A lung and nasal cavity tissues were isolated for biopsy, then fixed with 4% neutral buffered formalin, and then frozen. By using a cryostat, said frozen tissues were cut into a 10-μm cross-section, and stained with hematoxylin and eosin (H&E) and periodic acid Schiff reaction (PAS).

Also, indicators related to anti-rhinitis and anti-asthma effects were analyzed from the nasal cavity, serum, the BALF and lung tissues by using various analysis methods of Example 3 above, etc. Particularly, the indicators of the nasal cavity and serum were measured by means of an ELISA kit, and the indicators related to rhinitis and asthma of the BALF and lung tissues were measured by means of qRT-PCR, using primers of the table 14 above.

(2) Experimental Results

When the mice were treated with the OVA, a score of rhinitis symptoms (the number of sneezing and nasal rubbing behaviors) and allergic rhinitis symptoms including an expression of IL-4 and IL-5 in the nasal cavity were significantly increased. However, upon treatment with IM55 or IM76, a level of allergic rhinitis symptoms and IL-4 and IL-5 in the nasal cavity caused by the OVA was significantly decreased (FIGS. 18 to 20). Also, in case of treatment with IM55 or IM76, a disruption of the nasal cavity caused by the OVA was alleviated, and an expansion of epithelial cells in the nasal cavity was relieved (FIG. 21).

Furthermore, as a result of histological examination, in case of an animal model with induced rhinitis, lung inflammations and edema were induced therefrom; an expression of IL-5 and GATA3 was increased; and an expression of IL-10 and FOXp3 was decreased. However, upon treatment with IM55 or IM76, a disruption of lung tissues and an expansion of epithelial cells caused by the OVA were inhibited; an expression of GATA3 and IL-5 was inhibited; and an expression of FOXp3 and IL-10 was increased (FIGS. 22 to 26).

Example 8. Evaluation of the Alleviation Effect of Mixed Lactic Acid Bacteria on Rhinitis and Asthma (3)

An evaluation was made not only for an effect of IM55 or IM76 alone, but also for an effect of IM55 and IM76 mixtures on alleviating rhinitis and asthma. Particularly, a score of rhinitis symptoms, a distribution rate (%) of eosinophil cells in the BALF, and an expression level of cytokines in blood were analyzed by means of the same method as in Example 3 above, etc.

In result, it was identified for a group dosed with a mixture of IM55 and IM76 at a ratio of 1:1, 1:3 and 1:9 that a score of inflammatory symptoms, checked with the number of sneezing and nasal rubbing behaviors, is decreased and an expression level of IL-5 in the nasal cavity is decreased (FIG. 27). Also, it was identified that an expression level of IL-5 in serum is decreased (FIG. 28).

From the experiment on a model with induced rhinitis in Examples 6 to 8 above, it might be seen that a mixture of *Bifidobacterium longum* IM55 and *Lactobacillus plantarum* IM76 shows an effect of preventing, alleviating and treating asthma and rhinitis.

Example 9. Effect of Normalization of Intestinal Microorganisms and Alleviation of Colitis Intestinal microorganisms, which have been recently reported to have an influence on the occurrence and deterioration of allergic diseases, are an important factor in the occurrence of allergic diseases. Thus, to identify a change of microorganisms in colon according to administration of novel lactic acid bacteria, an expression of cytokines and a change in intestinal microorganisms in the colon were analyzed with regard to an allergic rhinitis model of Example 7 above.

Particularly, 2 μg of RNA was isolated from colon tissues of said animal model by using Takara thermal cycler and SYBR premix. qPCR was performed by means of said RNA, and a primer used for the qPCR was the same as shown in the table 14 above.

As a result of the analysis, an expression of IL-4 and IL-5 was increased and an expression of IL-10 was decreased in the colon upon treatment with the OVA. However, upon treatment with IM55, IM76 or mixtures thereof, it was identified that an expression of IL-4 and IL-5 is decreased and an expression of IL-10 is increased (FIG. 29).

Also, after isolating the colon from said animal model, 100 ng of total DNA was isolated from colonic fluid of said animal model by using Takara thermal cycler and SYBER premix. qPCR was performed by means of said DNA, and a primer used for the qPCR was the same as shown in a following table 19.

TABLE 19

| Bacteria type | Primer type | Primer sequence (5'-3') |
| --- | --- | --- |
| Firmicutes | Forward (SEQ ID NO: 21) | GGAGYATGTGGTTTAATTCGAAGCA |
| | Reverse (SEQ ID NO: 22) | AGCTGACGACAACCATGCAC |
| Bacteroidetes | Forward (SEQ ID NO: 23) | AACGCGAAAAACCTTACCTACC |
| | Reverse (SEQ ID NO: 24) | TGCCCTTTCGTAGCAACTAGTG |
| Actinobacteria | Forward (SEQ ID NO: 25) | TGTAGCGGTGGAATGCGC |
| | Reverse (SEQ ID NO: 26) | AATTAAGCCACATGCTCCGCT |
| δ/γ-proteobacteria | Forward (SEQ ID NO: 27) | GCTAACGCATTAAGTRYCCCG |
| | Reverse (SEQ ID NO: 28) | GCCATGCRGCACCTGTCT |
| TM7 | Forward (SEQ ID NO: 29) | GCAACTCTTTACGCCCAGT |
| | Reverse (SEQ ID NO: 30) | GAGAGGATGATCAGCCAG |

As a result of the analysis, upon treatment with the OVA, a population of Firmicutes, Proteobacteria and TM7 was increased, and a population of Bacteroidetes and Actinobacteria was decreased, and thus a ratio of Firmicutes/*Bacteroides* (F/B) and Proteobacteria/Bacteroidetes (P/B) was increased. However, upon treatment with IM55, IM76 or mixtures thereof, it was identified that a group of Proteobacteria increased by the OVA is significantly inhibited, and a group of Bacteroidetes and Actinobacteria decreased by occurrence of rhinitis is recovered (FIG. 30).

From the results, it might be seen that IM55, IM76 and mixtures thereof not only normalize the changed intestinal microorganisms, but also show an effect of controlling, preventing, alleviating and treating colitis.

Example 10. Preparation for Pharmaceutical Compositions Containing Lactic Acid Bacteria, Etc In preparation for following pharmaceutical compositions, a *Bifidobacterium longum* IM55 culture product may be replaced with a *Bifidobacterium longum* IM55 strain itself, a crushed product thereof or an extract thereof. Also, in preparation for the following pharmaceutical compositions, the *Bifidobacterium longum* IM55 culture product may be replaced with a *Lactobacillus plantarum* IM76 strain itself, a crushed product thereof or an extract thereof. Moreover, the following pharmaceutical composition may further contain chitosan.

<10-1> Preparation for Powder

*Bifidobacterium longum* IM55 culture product 20 mg
Lactose 100 mg
Talc 10 mg

Said components were mixed and filled into an airtight pack to prepare powder.

<10-2> Preparation for Tablet

*Bifidobacterium longum* IM55 culture product 10 mg
Maize starch 100 mg
Lactose 100 mg
Magnesium stearate 2 mg Said components were mixed and compressed to prepare a tablet according to a conventional method for preparing tablets.

<10-3> Preparation for Capsule Preparation

*Bifidobacterium longum* IM55 culture product 10 mg
Crystalline cellulose 3 mg
Lactose 15 mg
Magnesium stearate 0.2 mg Said components were mixed, and then filled into a gelatin capsule to prepare a capsule preparation according to a conventional method for preparing capsule preparations.

<10-4> Preparation for Pill

*Bifidobacterium longum* IM55 culture product 10 mg
Lactose 150 mg
Glycerin 100 mg
Xylitol 50 mg Said components were mixed and prepared into a pill, each of which is 4 g, according to a conventional method.

<10-5> Preparation for Granules

*Bifidobacterium longum* IM55 culture product 15 mg
Soybean extract 50 mg
Glucose 200 mg
Starch 600 mg Said components were mixed, after which 100 mg of 30% ethanol was added thereinto, then dried at 60° C., then formed into granules, and then filled into a pack.

<10-6> Preparation for Injection

*Bifidobacterium longum* IM55 culture product 10 mg
Sodium metabisulfite 3.0 mg
Methylparaben 0.8 mg
Propylparaben 0.1 mg
Suitable amount of sterile distilled water for injection Said components were mixed, after which 2 ml thereof was filled into an ample, then sterilized, and then prepared into an injection.

Example 11. Preparation for Health Functional Foods Containing Lactic Acid Bacteria, Etc In preparation for following health functional foods, a *Bifidobacterium longum* IM55 culture product may be replaced with a *Bifidobacterium longum* IM55 strain itself, a crushed product thereof or an extract thereof. Also, in preparation for the following health functional foods, a *Bifidobacterium longum* IM55 culture product may be replaced with a *Lactobacillus plantarum* IM76 strain itself, a crushed product thereof or an extract thereof. Also, the following health functional foods may further contain chitosan.

<11-1> Preparation for Flour Food 0.5 parts by weight of the *Bifidobacterium longum* IM55 culture product was added into 100 parts by weight of flour, after which the resulting mixture was used to prepare bread, cake, cookies, cracker and noodles.

<11-2> Preparation for Dairy Products 0.5 parts by weight of the *Bifidobacterium longum* IM55 culture product was added into 100 parts by weight of milk, after which said milk was used to prepare various dairy products such as butter and ice cream.

<11-3> Preparation for Powder of Mixed Grains

Unpolished rice, barley, glutinous rice and adlay, which were pregelatinized and dried by means of a known method, were roasted, and then prepared into powder of 60 mesh particle size with a grinder.

Black bean, black sesame and perilla seed, which were steamed and dried by means of a known method, were also roasted, and then prepared into powder of 60 mesh particle size with a grinder.

Said prepared grains, seeds and nuts, and *Bifidobacterium longum* IM55 culture product were compounded at a following ratio to prepare powder of mixed grains.

Grains (30 parts by weight of unpolished rice, 17 parts by weight of adlay and 20 parts by weight of barley);

Seeds and nuts (7 parts by weight of perilla seed, 8 parts by weight of black bean and 7 parts by weight of black sesame);

*Bifidobacterium longum* IM55 culture product (i part by weight);

*Ganoderma lucidum* (0.5 parts by weight); and

*Rehmannia glutinosa* (0.5 parts by weight)

<11-4> Preparation for Healthy Drink

Minor ingredients such as high fructose corn syrup (0.5 g), oligosaccharide (4 g), sugar (2 g), culinary salt (0.5 g) and water (77 g) as well as 1 g of the *Bifidobacterium longum* IM55 culture product were homogeneously compounded, then flash pasteurized, and then packed into each of small packing containers such as glass bottle, PET bottle, etc., to prepare healthy drink.

<11-5> Preparation for Vegetable Juice 2 g of the *Bifidobacterium longum* IM55 culture product was added into 1,000 ml of tomato or carrot juice to prepare vegetable juice.

<11-6> Preparation for Fruit Juice 1 g of *Bifidobacterium longum* IM55 culture product was added into 1,000 me of apple or grape juice to prepare fruit juice.

6. Accession Information of Lactic Acid Bacteria

The present inventors deposited *Bifidobacterium longum* IM55 for the purpose of patent to the Korean Culture Center of Microorganisms, a certified depository institution (address: Yulim Building, 45, Hongjenae 2ga-gil, Seodaemun-gu, Seoul, South Korea) on Jan. 20, 2017, and received an accession number of KCCM11961P. Also, the present inventors deposited *Lactobacillus plantarum* IM76 for the purpose of patent to the Korean Culture Center of Microorganisms, a certified depository institution (address: Yulim Building, 45, Hongjenae 2ga-gil, Seodaemun-gu, Seoul, South Korea) on Jan. 20, 2017, and received an accession number of KCCM11962P. Deposition of said lactic acid bacteria was performed in compliance with Budapest Treaty on the International Recognition of the Deposit of Micro-organism for the Purposes of Patent Procedure.

As shown above, the present invention has been described through Examples above, but is not necessarily limited thereto, and may be variously modified without departing from the scope and spirit of the present invention. Thus, the scope of protection of the present invention is to be interpreted to include all the embodiments belonging to the scope of patent claims attached to the present invention.

This application contains references to amino acid sequences and/or nucleic acid sequences which have been submitted concurrently herewith as the sequence listing XML file entitled "000332uscoa_SequenceListing.XML", file size 29 kilobytes, created on 20 Apr. 2023. The aforementioned sequence listing is hereby incorporated by reference in its entirety pursuant to 37 C.F.R. § 1.52 (e) (5).

[Accession Number]

Depository institution name: Korean Culture Center of Microorganisms (overseas)

Accession number: KCCM11961P

Accession date: 20170120

Depository institution name: Korean Culture Center of Microorganisms (overseas)

Accession number: KCCM11962P

Accession date: 20170120

The invention claimed is:

1. A method for treating allergic diseases, autoimmune diseases or inflammatory diseases, comprising:

administering an effective amount of a pharmaceutical composition comprising *Lactobacillus plantarum* strain IM76 deposited under accession number KCCM11962P to an individual in need thereof.

2. The method according to claim 1, wherein the *Lactobacillus plantarum* strain IM76 deposited under accession number KCCM11962P comprises a 16S rDNA sequence of SEQ ID NO: 2.

3. The method according to claim 1, wherein the *Lactobacillus plantarum* strain IM76 deposited under accession number KCCM11962P is a live cell body thereof, a dead cell body thereof, a crushed product thereof, or an extract thereof.

4. The method according to claim 1, wherein the allergic diseases are at least one selected from the group consisting of rhinitis, atopy, asthma, atopic dermatitis, allergic conjunctivitis, allergic otitis media, hives and anaphylactic shock.

5. The method according to claim 1, wherein the autoimmune diseases are at least one selected from the group consisting of Crohn's disease, rheumatoid arthritis, Hashimoto's thyroiditis, pernicious anemia, Addison's disease, type 1 diabetes, lupus, chronic fatigue syndrome, fibromyalgia syndrome, hypothyroidism and hyperthyroidism, scleroderma, Behcet's disease, inflammatory bowel disease, multiple sclerosis, myasthenia gravis, Meniere's syndrome, Guillain-Barre syndrome, Sjogren's syndrome, leukoplakia, endometriosis, psoriasis, leukoplakia, systemic scleroderma, asthma and ulcerative colitis.

6. The method according to claim 1, wherein the inflammatory diseases are at least one selected from the group consisting of arthritis, gout, hepatitis, obesity, corneitis, gastritis, enteritis, nephritis, diabetes, tuberculosis, bronchitis, pleurisy, peritonitis, spondylitis, pancreatitis, inflammatory pain, urethritis, cystitis, vaginitis, arteriosclerosis, septicemia, burn, dermatitis, periodontitis, gingivitis and colitis.

7. The method according to claim 1, wherein the pharmaceutical composition further comprises at least one prebiotic selected from the group consisting of chitosan, inulin and citrus pectin.

8. A method for alleviating allergic diseases, autoimmune diseases or inflammatory diseases, comprising administering an effective amount of a food composition comprising *Lactobacillus plantarum* strain IM76 deposited under accession number KCCM11962P to an individual in need thereof.

9. The method according to claim 8, wherein the *Lactobacillus plantarum* strain IM76 deposited under accession number KCCM11962P comprises a 16S rDNA sequence of SEQ ID NO: 2.

10. The method according to claim 8, wherein the *Lactobacillus plantarum* strain IM76 deposited under accession number KCCM11962P is a live cell body thereof, a dead cell body thereof, a crushed product thereof, or an extract thereof.

11. The method according to claim 8, wherein the allergic diseases are at least one selected from the group consisting of rhinitis, atopy, asthma, atopic dermatitis, allergic conjunctivitis, allergic otitis media, hives and anaphylactic shock.

12. The method according to claim 8, wherein the autoimmune diseases are at least one selected from the group consisting of Crohn's disease, rheumatoid arthritis, Hashimoto's thyroiditis, pernicious anemia, Addison's disease, type 1 diabetes, lupus, chronic fatigue syndrome, fibromyalgia syndrome, hypothyroidism and hyperthyroidism, scleroderma, Behcet's disease, inflammatory bowel disease, multiple sclerosis, myasthenia gravis, Meniere's syndrome, Guillain-Barre syndrome, Sjogren's syndrome, leukoplakia, endometriosis, psoriasis, leukoplakia, systemic scleroderma, asthma and ulcerative colitis.

13. The method according to claim 8, wherein the inflammatory diseases are at least one selected from the group consisting of arthritis, gout, hepatitis, obesity, corneitis, gastritis, enteritis, nephritis, diabetes, tuberculosis, bronchitis, pleurisy, peritonitis, spondylitis, pancreatitis, inflammatory pain, urethritis, cystitis, vaginitis, arteriosclerosis, septicemia, burn, dermatitis, periodontitis, gingivitis and colitis.

14. The method according to claim 8, wherein the food composition further comprises at least one prebiotic selected from the group consisting of chitosan, inulin and citrus pectin.

* * * * *